United States Patent
Lee et al.

(10) Patent No.: US 7,816,137 B2
(45) Date of Patent: Oct. 19, 2010

(54) METHOD FOR ISOLATING AND CULTURING MULTIPOTENT PROGENITOR CELLS FROM UMBILICAL CORD BLOOD

(75) Inventors: Myoung Woo Lee, Bucheon-si (KR); Young Jin Kim, Donga Apt. 102-2004, Jamwon-dong, Seocho-gu, Seoul (KR) 137-948; Jeong Eun Choi, Seongnam-si (KR); Mal Sook Yang, Suwon-si (KR); Young Joon Moon, Seoul (KR); Sun Kyung Kim, Hwaseong-si (KR); Hugh Chul Kim, Suwon-si (KR); Joon Seong Park, Suwon-si (KR); In Keun Jang, Suwon-si (KR)

(73) Assignees: Lifecord Inc., Seoul (KR); Young Jin Kim, Seoul (KR)

( * ) Notice: Subject to any disclaimer, the term of this patent is extended or adjusted under 35 U.S.C. 154(b) by 966 days.

(21) Appl. No.: 10/587,398

(22) PCT Filed: Jan. 31, 2005

(86) PCT No.: PCT/KR2005/000278

§ 371 (c)(1),
(2), (4) Date: Jul. 27, 2006

(87) PCT Pub. No.: WO2005/073366

PCT Pub. Date: Aug. 11, 2005

(65) Prior Publication Data

US 2007/0122902 A1     May 31, 2007

(30) Foreign Application Priority Data

Jan. 30, 2004  (KR)  ............... 10-2004-0006088
Jan. 25, 2005  (KR)  ............... 10-2005-0006595

(51) Int. Cl.
*C12N 5/00*     (2006.01)

(52) U.S. Cl. ............... 435/377; 435/325; 435/375

(58) Field of Classification Search ............... None
See application file for complete search history.

(56) References Cited

U.S. PATENT DOCUMENTS

| 4,190,535 | A | * | 2/1980 | Luderer et al. | 210/789 |
| 5,004,681 | A | * | 4/1991 | Boyse et al. | 435/2 |
| 5,652,225 | A | * | 7/1997 | Isner | 514/44 R |
| 6,069,005 | A | * | 5/2000 | Reid et al. | 435/325 |
| 2002/0028510 | A1 | | 3/2002 | Sanberg et al. | |
| 2002/0115059 | A1 | | 8/2002 | Terada et al. | |
| 2003/0211602 | A1 | * | 11/2003 | Atala | 435/366 |
| 2005/0148072 | A1 | * | 7/2005 | Reid et al. | 435/370 |

FOREIGN PATENT DOCUMENTS

| KR | 20030069115 A | 6/2003 |
| WO | 9640116 A1 | 12/1996 |
| WO | 9920741 A1 | 4/1999 |
| WO | 9947646 A1 | 9/1999 |
| WO | 0151616 A2 | 7/2001 |
| WO | 0216560 A1 | 2/2002 |
| WO | 02064755 A2 | 8/2002 |
| WO | 03042405 A2 | 5/2003 |
| WO | 03/055989 A2 | 7/2003 |
| WO | 03068937 A2 | 8/2003 |
| WO | 03070922 A1 | 8/2003 |

OTHER PUBLICATIONS

Pittenger MP et al. 1999. Multilineage potential of adult human mesenchymal stem cells. Science 284: 143-147.*
M. Reyes, et al., Purification and ex vivo expansion of postnatal human marrow mesodernal progenitor cells, In: Blood, Nov. 1, 2001, vol. 98(9), pp. 2615-2625.

* cited by examiner

*Primary Examiner*—Lora E Barnhart
(74) *Attorney, Agent, or Firm*—Sughrue Mion, PLLC

(57) ABSTRACT

Since the multipotent progenitor/stem cells isolated and cultured from the cord blood-derived mononuclear cells according to the method of the present invention are capable of differentiating into several types of cells including neurons, osteoblasts, myoblasts, endothelial cells, hepatocytes and dendritic cells, they can be effectively used for a cell therapy, a cell restoration technique or an organ production.

4 Claims, 17 Drawing Sheets

METHOD FOR ISOLATING AND CULTURING MULTIPOTENT PROGENITOR CELLS FROM UMBILICAL CORD BLOOD

This is a national stage application under 35 U.S.C. §371 of PCT/KR2005/000278 filed on Jan. 31, 2005, which claims priority from Korean patent application 10-2004-0006088 filed on Jan. 30, 2004, and from Korean patent application 10-2005-0006595 filed on Jan. 25, 2005, all of which are incorporated herein by reference.

FIELD OF THE INVENTION

The present invention relates to a method for isolating and culturing multipotent progenitor/stem cells from mononuclear cells derived from umbilical cord blood and methods for inducing differentiation of the multipotent progenitor/stem cells into various types of cells.

BACKGROUND OF THE INVENTION

Stem cells have multi-differentiation potency to differentiate into cells of various tissues by specific differentiation-inducing stimuli as well as self-renewal capacity at the in undifferentiation stage. They are divided into embryonic stem cells (ES cells) and adult stem cells depending on their differentiation potency and time to be generated. ES cells are isolated from the inner cell mass (ICM) of embryos at the blastocyst stage. ES cells include three types of germ layers, i.e., endoderm, mesoderm and ectoderm, and are pluripotent cells that are capable of differentiating into virtually every type of cells found in an organism. However, there still remain difficulties involved in how to control their differentiation potency as well as the problem of ethics.

In contrast, adult stem cells appear at the stage of organ formation during the embryonic development or at the adult stage. They are organ-specific and multipotent, i.e., they are generally committed to give rise to cells constituting a specific organ. These adult stem cells remain in most of adult organs and perform the critical role of continually replenishing the loss of cells occurring normally or pathologically.

Representative adult stem cells include hematopoietic stem cells (HSCs) and mesenchymal stem cells (MSCs) present in bone marrow. HSCs give rise to various blood cells such as erythrocytes, leukocytes and thrombocytes; and MSCs, to the cells of mesodermal tissues such as osteoblasts, chondroblasts, adipocytes and myoblasts.

Since the successful isolation of human embryonic stem cells or adult stem cells was reported, clinical applications of the stem cells have drawn increasing interests. The most noticeable potential application of the stem cells is their use as a cell supply source for cell replacement therapy. Hard-to cure diseases, e.g., neurodegenerative disease such as Parkinson's and Alzheimer's diseases, quadriplegia resulting from spinal cord injury, leukemia, apoplexy, juvenile-onset diabetes, cardiac infarction, hepatocirrhosis and other chronic diseases, are caused by the disruption and permanent functional disorder of the cells constituting certain organs. Cell replacement therapy by which the loss of cells is replenished from the outside has been presented as a promising remedy therefor.

ES stem cells can be obtained from bone marrow, and it has been reported that HSCs, MSCs and multipotent adult progenitor cells (MAPCs) exists in bone marrow. Several reports have demonstrated that MAPCs derived from bone marrow can differentiate into cells of other tissues such as nerve cells, endothelial cells and hepatocytes as well as into osteoblasts, chondroblasts and adipocytes similar to MSCs (Reyes M, et al., *Blood* 98: 2615-2625, 2001; Reyes M, et al., *J. Clin. Invest.* 109: 337-346, 2002). However, notwithstanding the remarkable effect expected of the cell replacement therapy using bone marrow-derived stem cells, there exist many limitations in its clinical applications. For example, the conventional method for isolating stem cells from bond marrow has the problem of requiring several steps of complicated operations, which may impose mental and physical stress on a donor. Further, it is very difficult to find a donor for bone marrow transplantation who has an antigen phenotype identical to a recipient.

Since the presence of MSCs in bone marrow was discovered by Friedenstein (Friedenstein A J, *Int. Rev. Cytol.* 47: 327-345, 1976), there have been numerous studies on their differentiation potency and use as a cell therapeutic agent. Especially, the clinical use of MSCs for the treatment of cartilaginous diseases is in the process of regulatory approval, and a therapeutic agent comprising the same for treating osteocyte-relating diseases is about to enter a clinical stage. However, MSCs in bone marrow have a limitation in their applicable targets due to their restricted differentiation and proliferation potencies, and they are still not free from the previously reported problems in obtaining bone marrow-derived stem cells. Further, MAPCs derived from bone marrow show a wide applicable range in terms of differentiation potency, but they also have problems in how to reproducibly isolate and cultivate besides the limitations imposed by the bone marrow origin.

Meanwhile, as it has been reported that umbilical cord blood contains a large quantity of stem cells and is a source of HSCs, there have been made several attempts to clinically remedy blood disorders by cord blood transplantation. Further, cord blood transplantation triggers a much lower degree of graft-host rejective interaction than bone marrow transplantation, and extensive studies for its clinical use have been carried out.

However, there still remain problems in the isolation and cultivation of MSCs in cord blood (Erices A, et al., *Br. J. Haematol.* 109: 235-242, 2000; Lee O K, et al., *Blood* 103: 1669-1675, 2004; Wexler S A, et al., *Br. J. Haematol.* 121: 368-74, 2003). Also, there is no report on a reliable method for isolating and culturing stem cells capable of differentiating into various types of cells such as neurons, osteoblasts, myoblasts, adipocytes and so on from cord blood.

The present inventors have endeavored to develop a method for obtaining multipotent progenitor/stem cells that can be effectively used for cell therapy, cell replacement therapy, an organ restoration technique, or an organ production, and have established effective methods for isolating and culturing multipotent progenitor/stem cells from mononuclear cells derived from cord blood, and differentiating the multipotent progenitor/stem cells into various types of cells such as neurons, osteoblasts, myoblasts, endothelial cells, hepatocytes and dendritic cells.

SUMMARY OF THE INVENTION

Accordingly, it is an object of the present invention to provide a method for isolating and culturing multipotent progenitor/stem cells from mononuclear cells derived from cord blood, and methods for inducing differentiation of the multipotent progenitor/stem cells into various types of cells.

In accordance with one aspect of the present invention, there is provided a method for isolating and culturing multipotent progenitor/stem cells from cord blood-derived mononuclear cells, which comprises culturing the cord blood-derived mononuclear cells successively in:

1) a first animal cell culture medium comprising fetal bovine serum (FBS), L-glutamine and granulocyte macrophage-colony stimulating factor (GM-CSF), in addition to inorganic salts, vitamins, amino acids and/or supplementary elements;

2) a second animal cell culture medium which is the same as the first animal cell culture medium except for lacking GM-CSF; and 3) a third animal cell culture medium which is the same as the first animal cell culture medium except that GM-CSF is replaced with stem cell factor(SCF) and epidermal growth factor(EGF).

In accordance with another aspect of the present invention, there is provided a method for inducing differentiation of the multipotent progenitor/stem cells isolated and cultured by the above method into various types of cells and medium compositions used therein.

In accordance with a further aspect of the present invention, there is provided a cell composition for a cell therapy comprising the multipotent progenitor/stem cells isolated and cultured by the above method as an effective ingredient.

BRIEF DESCRIPTION OF THE DRAWINGS

The above and other objects and features of the present invention will become apparent from the following description of the invention, when taken in conjunction with the accompanying drawings, which respectively show.

A:×100, B:×200

Figure 2:
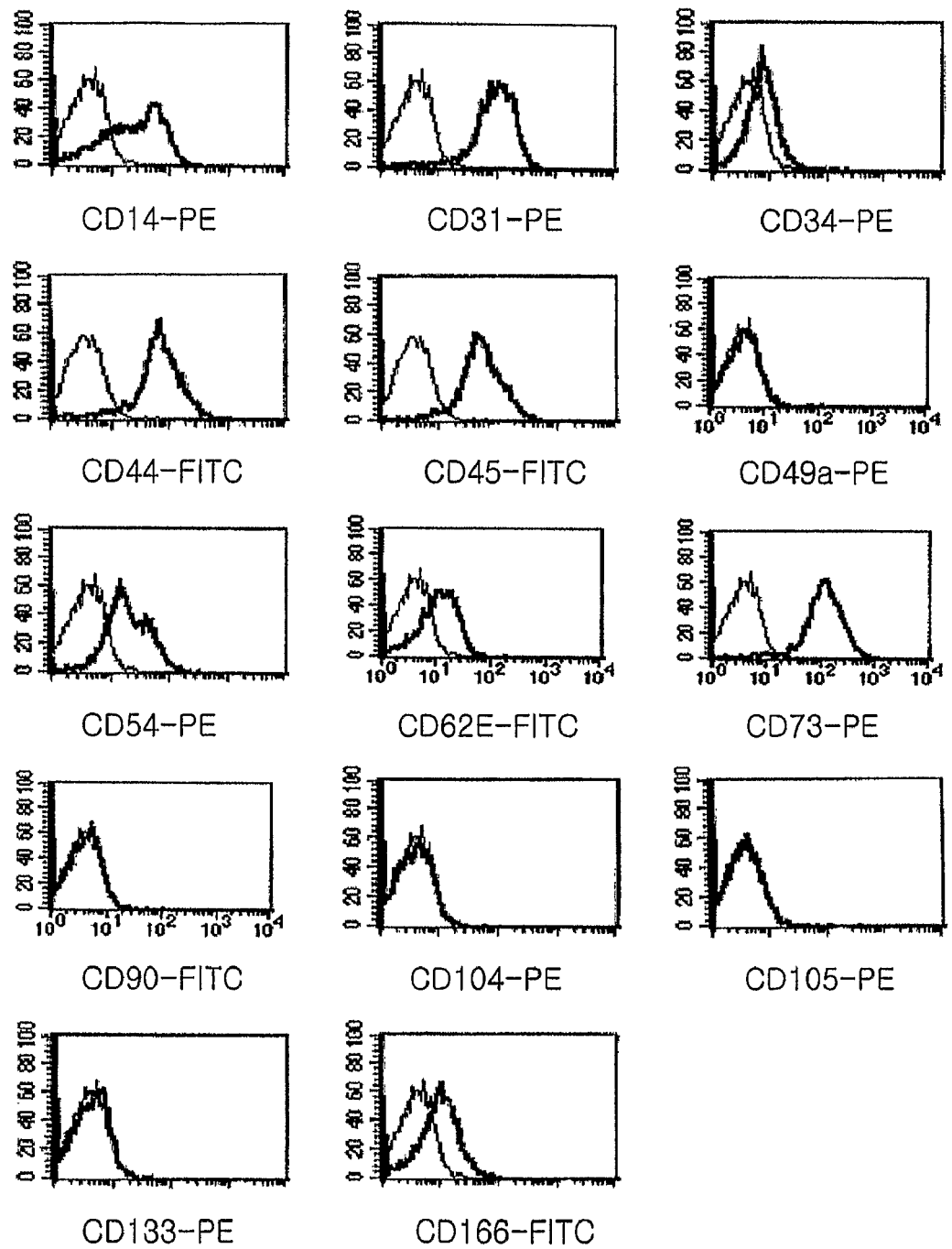
Figure 4:
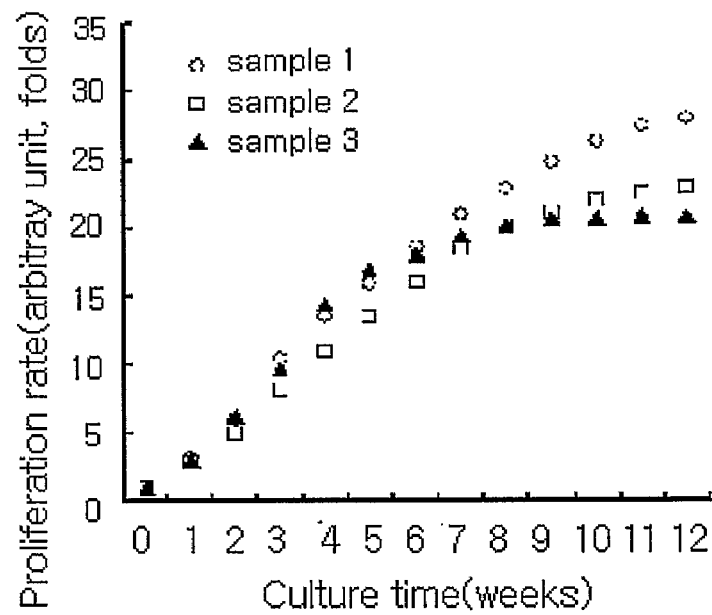
Figure 5:
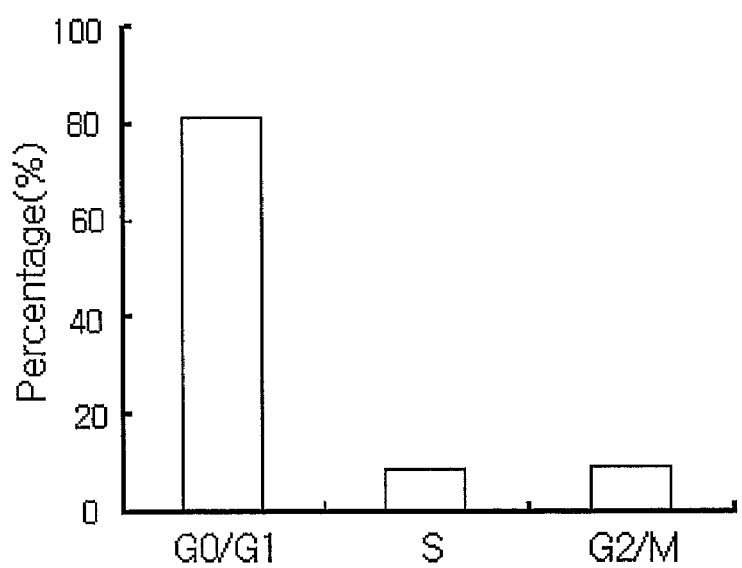
Figure 6:
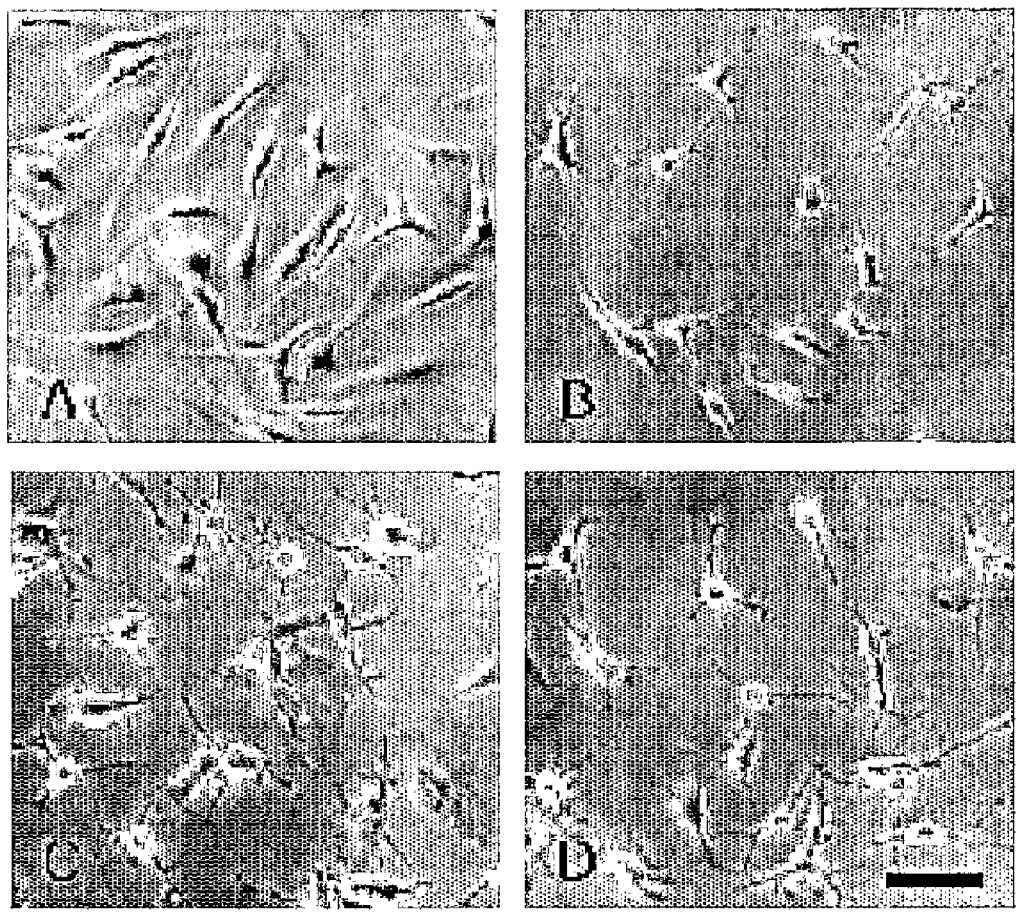
Figure 7:
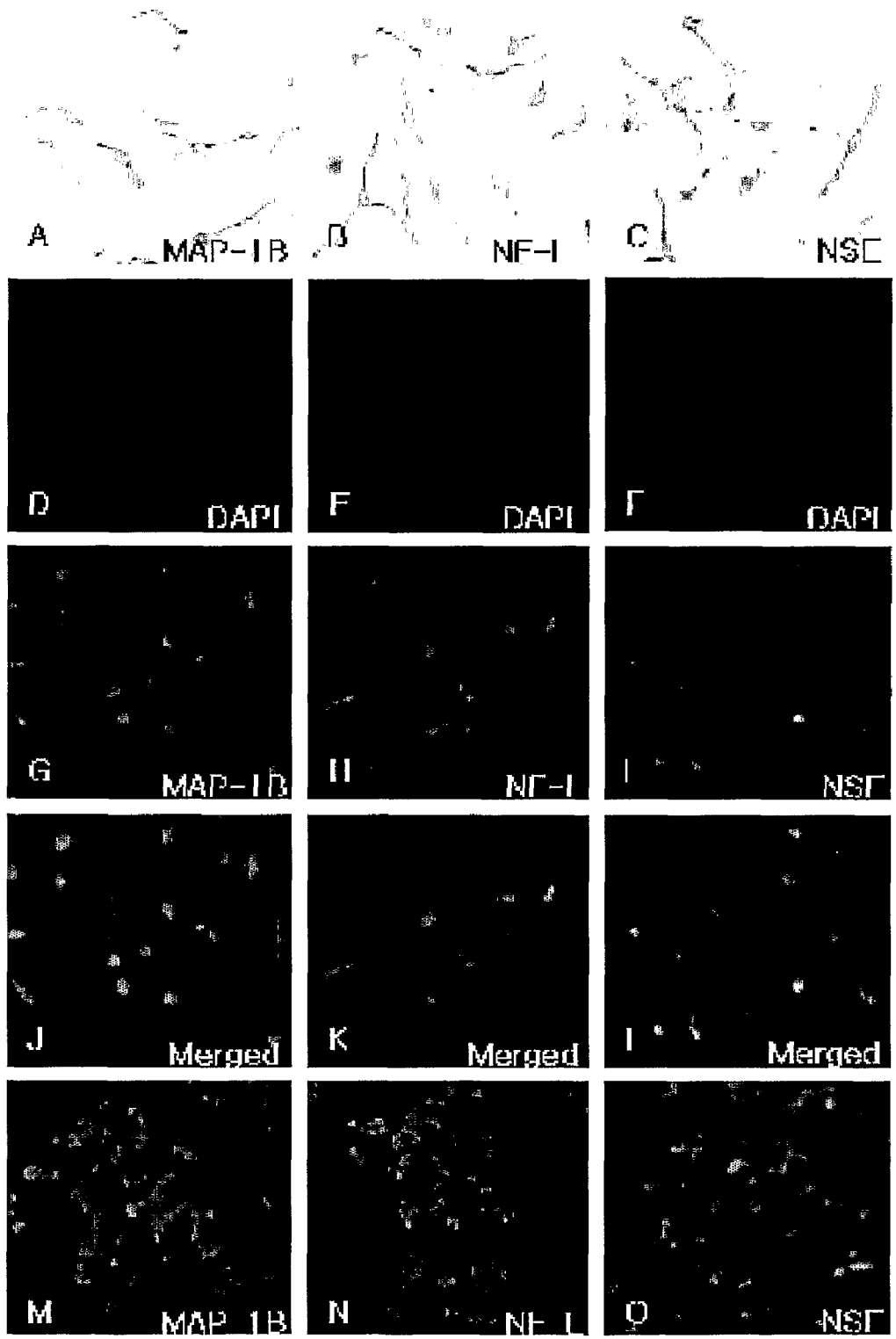

FIG. 2: the immunophenotype profile of the multipotent progenitor/stem cells isolated and cultured from the cord blood-derived mononuclear cells;

FIG. 3: the results of comparing inmunophenotype profiles of the multipotent progenitor/stem cells depending on a time course of cultivation;

FIG. 4: the graph showing survival rates of the multipotent progenitor/stem cells depending on a time course of cultivation;

FIG. 5: a cell cycle profile of the multipotent progenitor/stem cells isolated and cultured from the cord blood-derived mononuclear cells;

FIG. 6: photomicrographs of the neurons differentiated from the cord blood-derived multipotent progenitor/stem cells;

A: before the differentiation induction,
B: 3 days after the differentiation induction,
C: 7 days after the differentiation induction,
D: 14 days after the differentiation induction FIG. 7: the results of fluorescence-(G to I) or immunocytochemical staining (A to C) of the neurons differentiated from the cord blood-derived miultipotent progenitor/stem cells;

| A: MAP-1B staining, | B: NF-L staining, |
|---|---|
| C: NSE staining, | D: nucleus staining, |
| E: nucleus staining, | F: nucleus staining, |
| G: MAP-1B staining, | H: NF-L staining, |
| I: NSE staining, | J: overlap of D and G, |
| K: overlap of E and H, | L: overlap of F and I, |
| M: MAP-1B staining using IMR32 (neuroblastoma cell line, positive control), | |
| N: NF-L staining using IMR32 (positive control), | |
| O: NSE staining using IMR32 (positive control) | |

Figure 8:
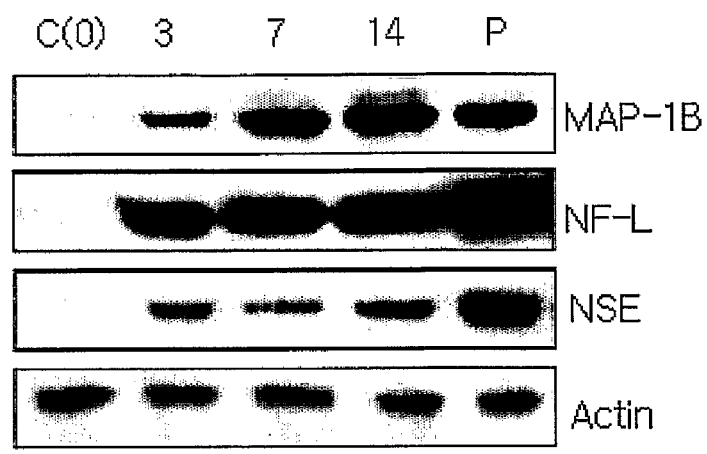

FIG. 8: the results of western blotting of the neurons differentiated from the cord blood-derived multipotent progenitor/stem cells;

C (0): before the differentiation induction,
3: 3 days after the differentiation induction,
7: 7 days after the differentiation induction,
14: 14 days after the differentiation induction,
P: IMR32(positive control)

Figure 9:
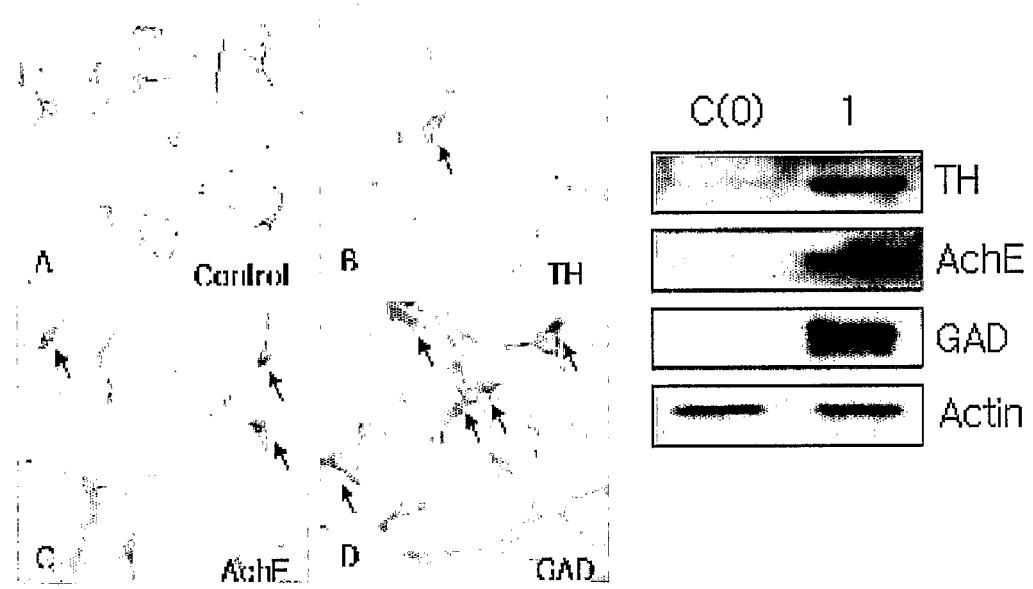
Figure 10:
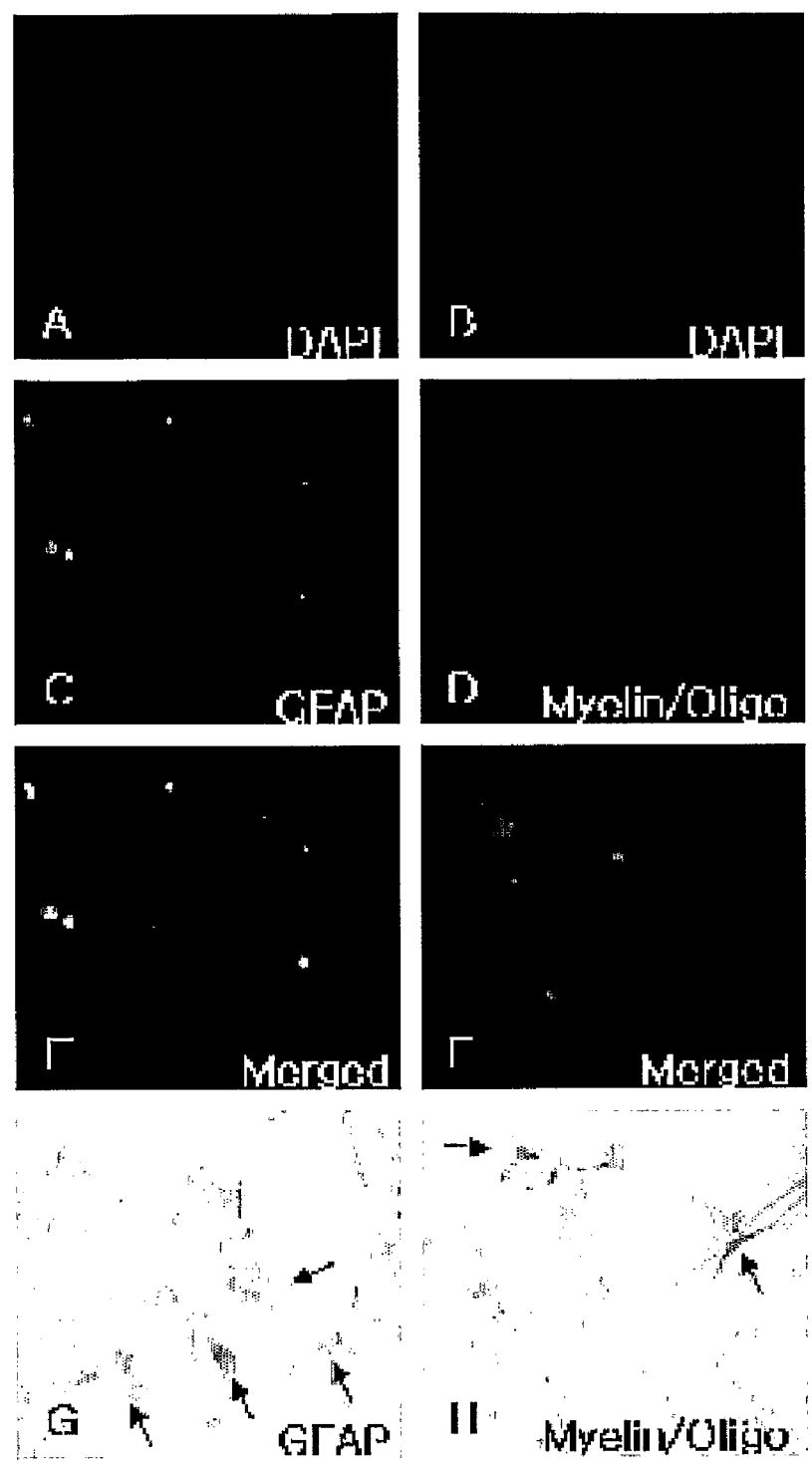

FIG. 9: the results of analyzing cell types of the neurons differentiated from the cord blood-derived multipotent progenitor/stem cells by immunocytochemical staining and western blotting;

A: undifferentiated (positive control),
B: TH staining (dopaminergic neurons),
C: AchE staining (chollinergic neurons),
D: GAD staining (gabanergic neurons),
E: western blotting,
C (0): before the differentiation induction,
I: 14 days after the differentiation induction FIG. 10: the results of fluorescence-(C and D) or immunocytochemical staining (G and H) of the neuroglial cells differentiated from the cord blood-derived multipotent progenitor/stem cells;

| A: nucleus staining, | B: nucleus staining, |
|---|---|
| C: GFAP staining, | D: myelin/oligodendrocyte staining, |
| E: overlap of A and C, | F: overlap of B and D, |
| G: GFAP staining, | H: myelin/oligodendrocyte staining, |

Figure 11:
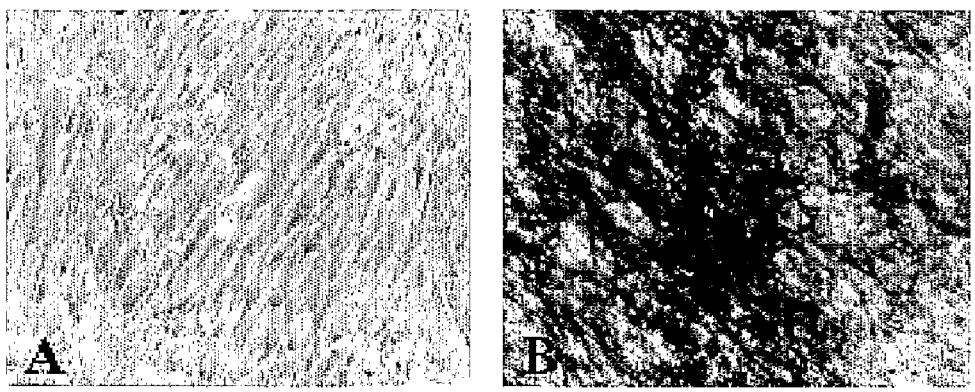
Figure 12:
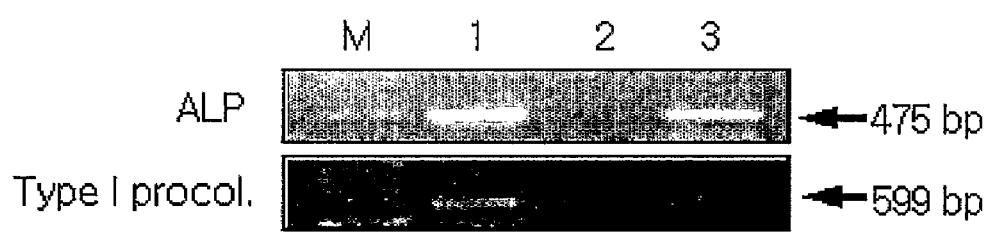
Figure 13:
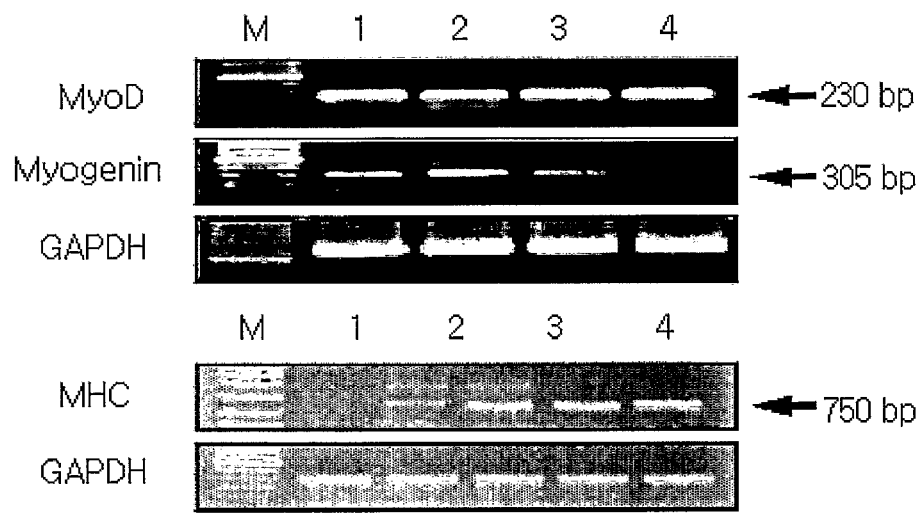
Figure 14:
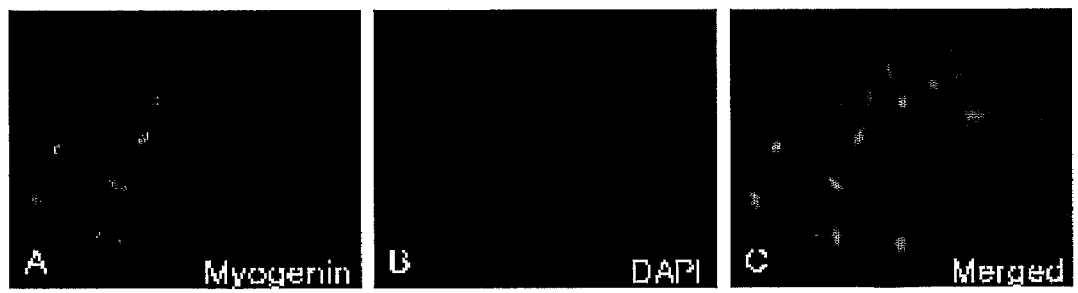

FIG. 11: the results of microscopic observation (A) and alkaline phosphatase (ALP) staining (B) of the osteoblasts differentiated from the cord blood-derived multipotent progenitor/stem cells, FIG. 12: the results of RT-PCR of the osteoblasts differentiated from the cord blood-derived multipotent progenitor/stem cells;

M: molecular weight marker,
1: osteoblasts differentiated from bone marrow-derived mesenchymal stem cells (positive control),
2: before the differentiation induction,
3: after the differentiation induction FIG. 13: the results of RT-PCR of the myoblasts differentiated from the cord blood-derived multipotent progenitor/stem cells;

M: molecular weight marker,
1: 1 week after the differentiation induction,
2: 2 weeks after the differentiation induction,
3: 3 weeks after the differentiation induction,
4: 4 weeks after the differentiation induction,
5: 5 weeks after the differentiation induction FIG. 14: the results of fluorescence immunocytochemical staining of the myoblasts differentiated from the cord blood-derived multipotent progenitor/stem cells;

| A: myogenin staining, | B: nucleus staining, |
|---|---|
| C: overlap of A and B | |

Figure 15:
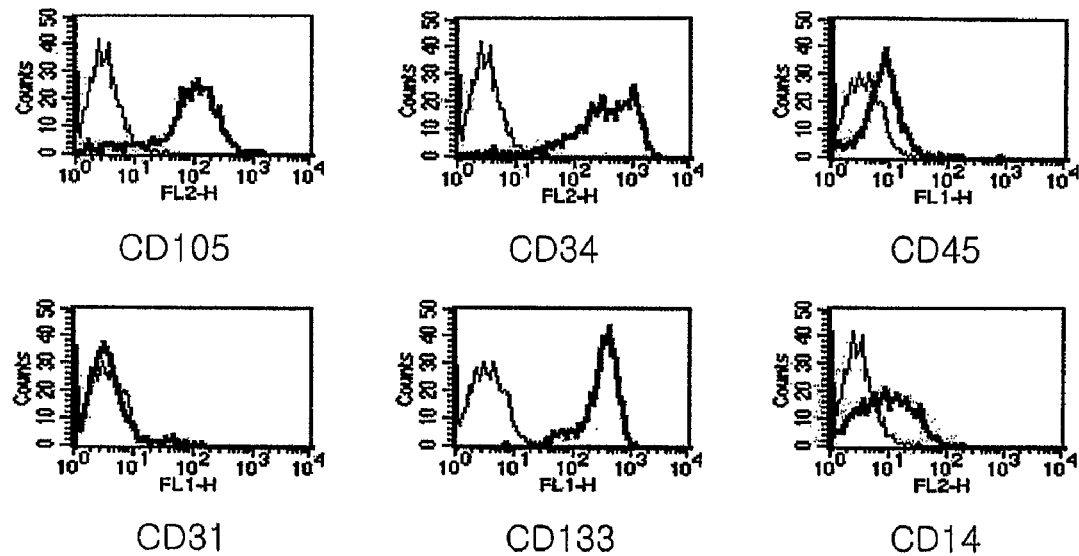
Figure 16:
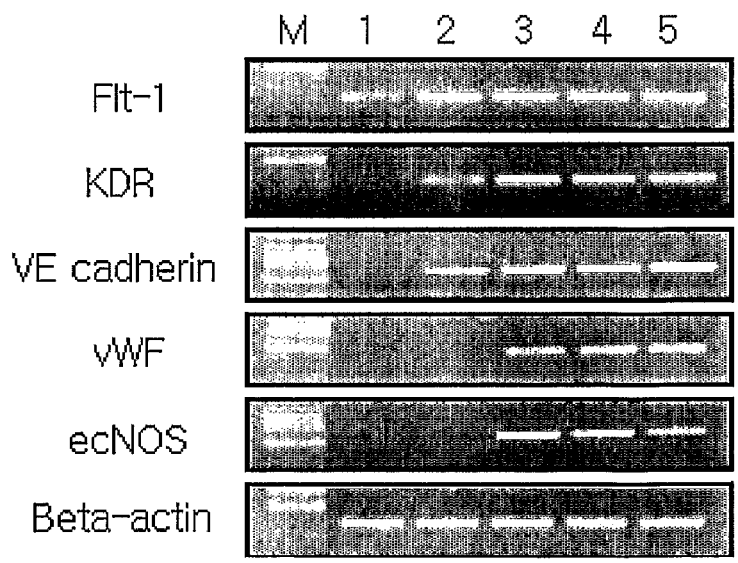

FIG. 15: the immunophenotype profile of the endothelial cells differentiated from the cord blood-derived multipotent progenitor/stem cells;

FIG. 16: the results of RT-PCR of the endothelial cells differentiated from the cord blood-derived multipotent progenitor/stem cells;

M: molecular weight marker,
1: before the differentiation induction,
2: 3 days after the differentiation induction,
3: 7 days after the differentiation induction,
4: 14 days after the differentiation induction,
5: HUVEC (human umbilical vein endothelial cells, positive control)

Figure 17:
Figure 18:
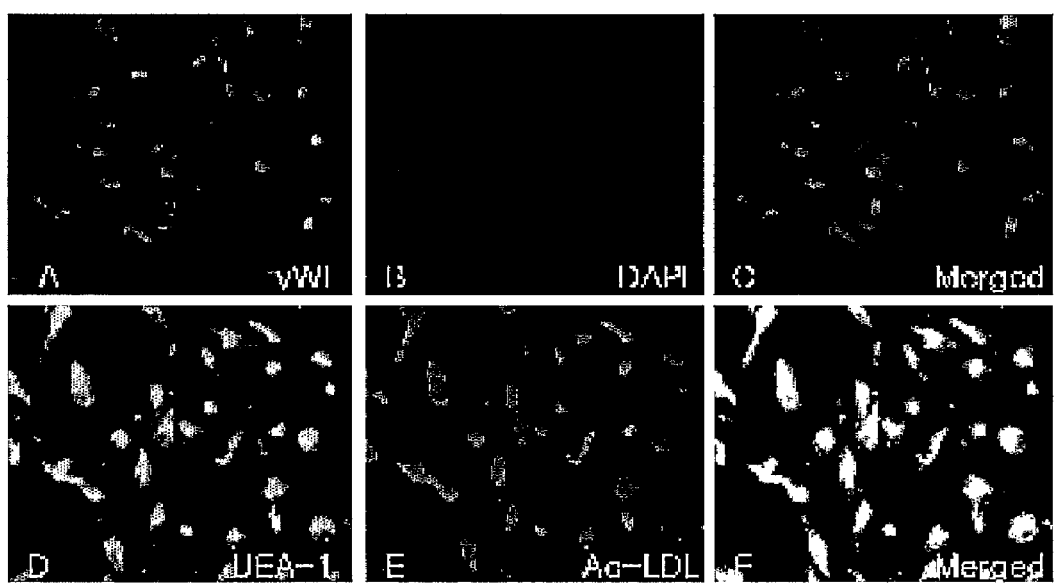

FIG. 17: the results of western blotting of the endothelial cells differentiated from the cord blood-derived multipotent progenitor/stem cells;

7: 7 days after the differentiation induction,
14: 14 days after the differentiation induction,
HUVEC: positive control FIG. 18: the results of fluorescence immunocytochemical staining of the endothelial cells differentiated from the cord blood-derived multipotent progenitor/stem cells;

| A: vWF staining, | B: nucleus staining, |
| C: overlap of A and B, | D: UEA-1 staining, |
| E: Ac-LDL uptake, | F: overlap of D and E |

Figure 19:
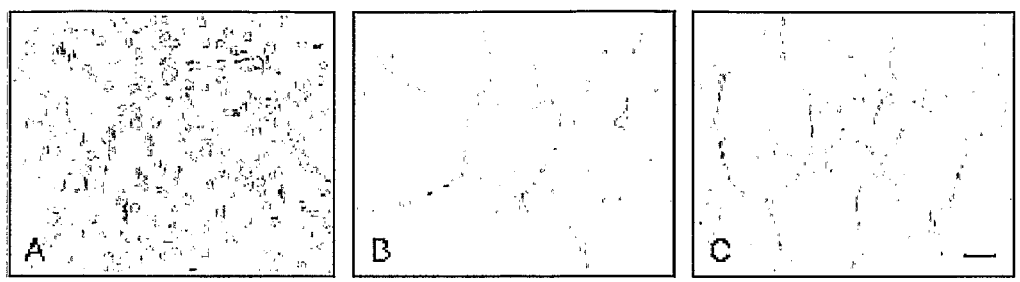

FIG. 19: the results of examining tube formation activity of the endothelial cells differentiated from the cord blood-derived multipotent progenitor/stem cells;

A: before the differentiation induction,
C: tube formation using HUVEC (positive control)

Figure 20:
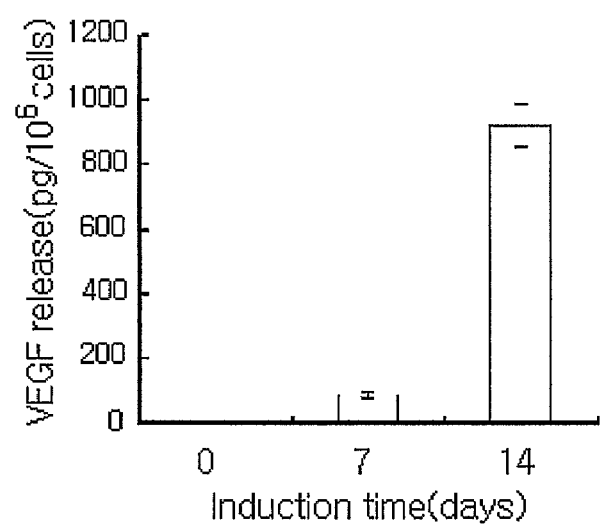
Figure 21:
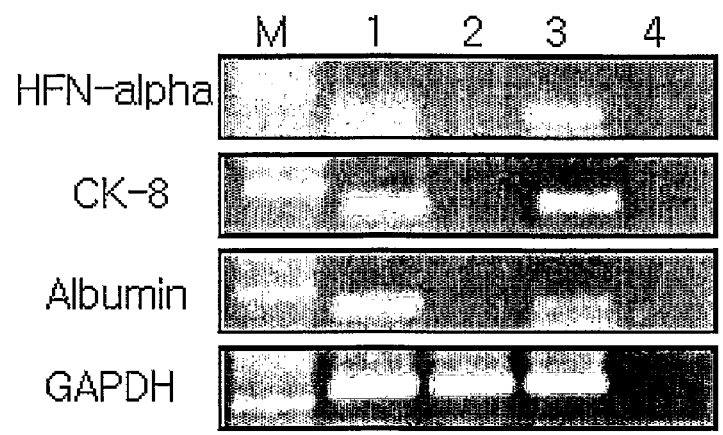
Figure 22:
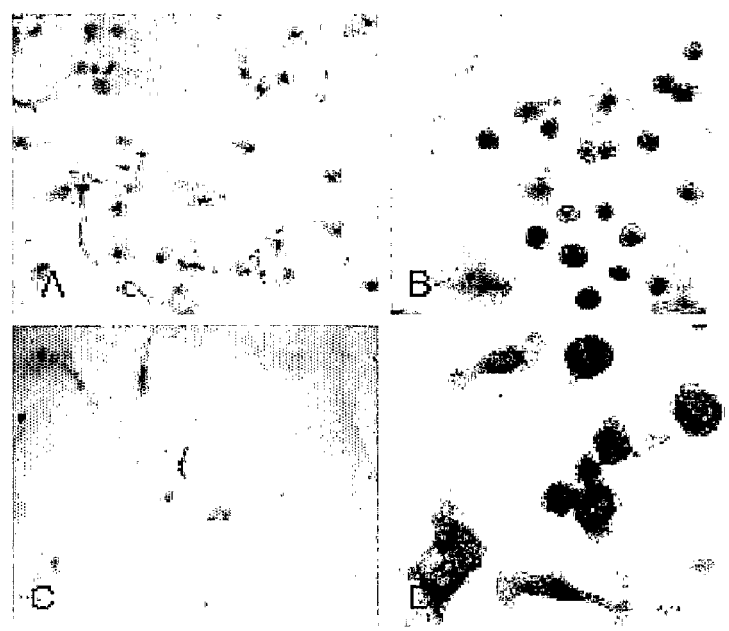
Figure 24:
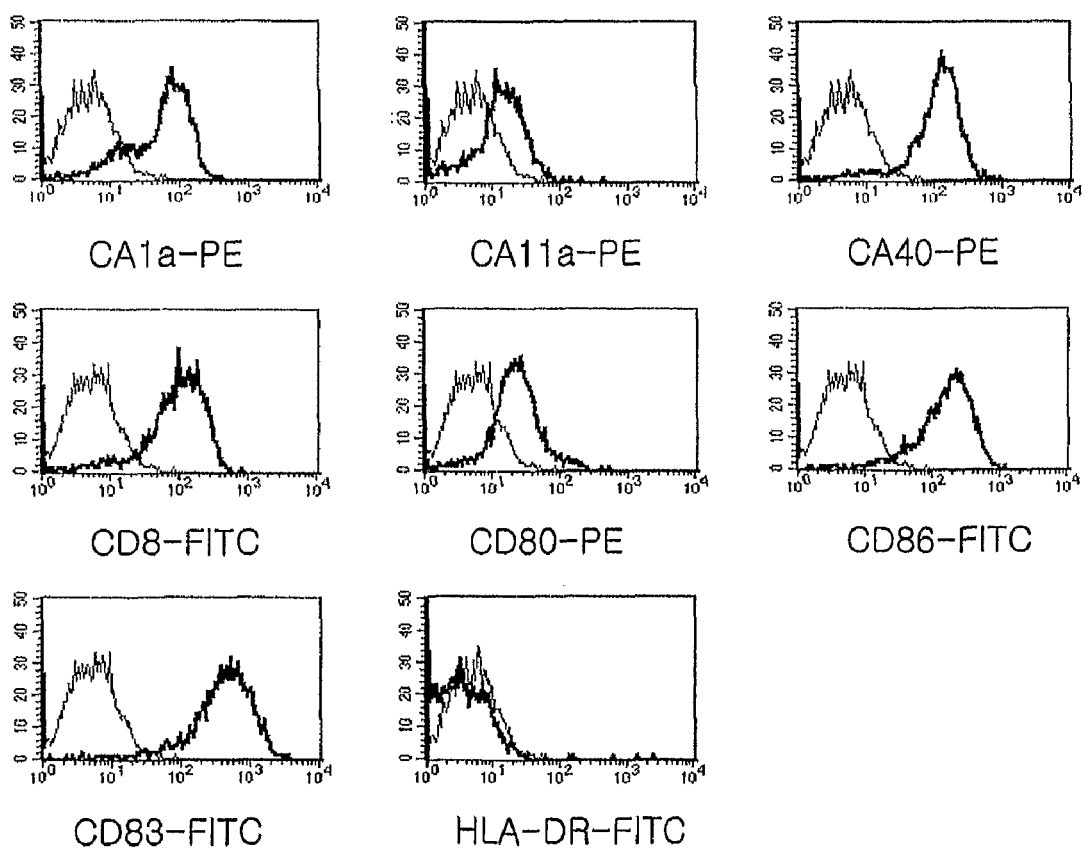
Figure 25:
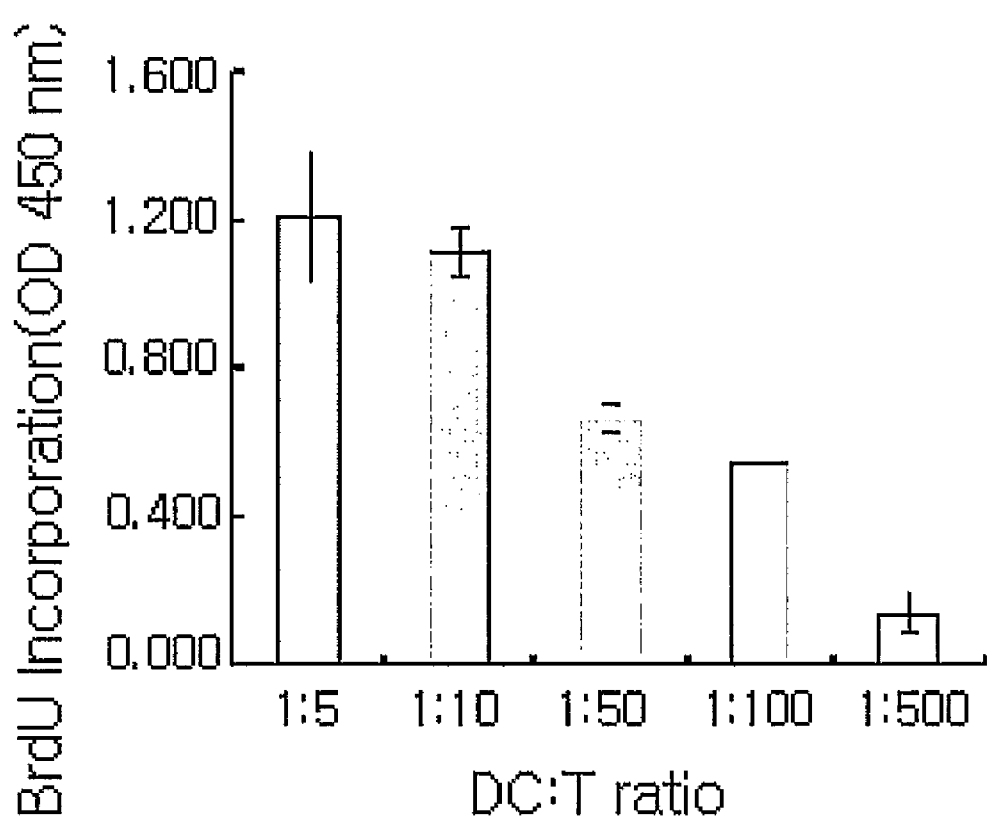

FIG. 20: the results of examining VEGE (vascular endothelial growth factor) secretion activity of the endothelial cells differentiated from the cord blood-derived multipotent progenitor/stem cells;

FIG. 21: the results of RT-PCR of the hepatocytes differentiated from the cord blood-derived multipotent progenitor/stem cells;

M: molecular weight marker,
1: HepG2(liver cancer cell line),
2: undifferentiated multipotent progenitor/stem cells,
3: hepatocytes differentiated from multipotent progenitor/stem cells,
4: negative control FIG. 22: the results of immunocytochemical staining of the hepatocytes differentiated from the cord blood-derived multipotent progenitor/stem cells;

A: CK-8 in undifferentiated multipotent progenitor/stem cells,
B: CK-8 in hepatocytes differentiated from multipotent progenitor/stem cells,
C: albumin in undifferentiated multipotent progenitor/stem cells,
D: albumin in hepatocytes differentiated from multipotent progenitor/stem cells FIG. 23: the result of examining dextran-FITC uptake rate of the immature dendritic cells differentiated from the cord blood-derived multipotent progenitor/stem cells;

FIG. 24: the results of immunophenotyping of the mature dendritic cells differentiated from the cord blood-derived multipotent progenitor/stem cells; and FIG. 25: the results of examining the effect on inducing T lymphocyte proliferation of the mature dendritic cells differentiated from the cord blood-derived multipotent progenitor/stem cells.

DETAILED DESCRIPTION OF THE INVENTION

As used herein, the term "animal cell culture medium" refers to a medium comprising inorganic salts, amino acids, vitamins and/or supplementary elements, which is conventionally used for culturing animal cells. Representative commercially available media for animal cell culture include, but are not limited to, DMEM (Dulbecco's Modified Eagle Medium), MEM (Minimum Essential Medium), IMDM (Iscove's Modified Dulbecco's Medium), α-MEM, RPMI 1640, and so on.

The term "high glucose medium" as used herein refers to an animal cell culture medium further containing D-glucose ranging from 3,500 to 5,500 mg/l and sodium pyruvate ranging from 50 to 200 mg/l. Representative commercially available high glucose media include, but are not limited to, HG(high glucose)-DMEM, IMDM and so on.

The term "a first animal cell culture medium" as used herein refers to an animal cell culture medium used at an initial step for isolating and culturing multipotent progenitor/stem cells from cord blood-derived mononuclear cells, which induces only multipotent progenitor/stem cells among several types of stem cells in cord blood to form a multi-layer cell colony. Preferably, the first animal cell culture medium is a high glucose medium further containing fetal bovine serum (FBS), L-glutamine and granulocyte macrophage-colony stimulating factor (GM-CSF).

The term "a second animal cell culture medium" as used herein refers to an animal cell culture medium for metamorphosing the multi-layer cell colony formed in the above first culture into a mono-layer cell colony. The second animal cell culture medium is the same as the first animal cell culture medium except that it lacks GM-CSF, preferably a high glucose medium containing additional FBS and L-glutamine.

The term "a third animal cell culture medium" as used herein refers to an animal cell culture medium for inducing proliferation of the cells forming the mono-layer cell colony cultured in the second animal cell culture medium. The third animal cell culture medium is the same as the first animal cell culture medium except that GM-CSF is replaced with stem cell factor (SCF) and epidermal growth factor (EGF), preferably a high glucose medium containing additional FBS, L-glutamine, SCF and EGF.

The present invention provides a method for isolating and culturing multipotent progenitor/stem cells from cord blood-derived mononuclear cells using a series of animal cell culture media.

In order to isolate and culture the multipotent progenitor/stem cells from the cord blood-derived mononuclear cells, it is preferred to culture the cord blood-derived mononuclear cells in the following animal cell culture media in order:

1) a first animal cell culture medium which is an animal cell culture medium further containing FBS, L-glutamine and GM-CSF;

2) a second animal cell culture medium which is the same as the first animal cell culture medium except for lacking GM-CSF; and 3) a third animal cell culture medium which is the same as the first animal cell culture medium except that GM-CSF is replaced with SCF and EGF.

Umbilical cord blood is blood retrieved from the vein of the umbilical cord which connects the placenta to the fetus in a mammalian including a human and collected before the detachment of placenta from the uterus after the delivery of a baby. It is preferred to use cord blood isolated from the human umbilical cord blood in the present invention.

For the isolation of mononuclear cells from cord blood, the common method well-known in the art such as Ficoll-Hypaque density gradient method can be employed.

In brief, cord blood thus isolated is diluted by mixing with a phosphate buffered saline (PBS), and the diluted cord blood is overlayed onto an equal volume of Ficoll-Hypaque solution (density; 1.077 g/ml). At this time, the Ficoll-Hypaque solution is pre-warmed at room temperature before use, and it is preferable to maintain the volume of diluted cord blood be low the 3-fold level of the Ficoll-Hypaque solution. The resulting mixture is subjected to centrifuigation to separate an erythrocyte layer, a mononuclear cell layer, and a serologic layer. Only the mononuclear cell layer is transferred to a new tube using a pasteur pipette and washed with PBS to remove contaminants such as the Ficoll-Hypaque solution and platelets.

The mononuclear cells thus isolated may be directly applied to the isolation and cultivation of multipotent progenitor/stem cells or stored in a deep freezer until use.

In order to isolate and culture multipotent progenitor/stem cells from the cord blood-derived mononuclear cells, the mononuclear cells are cultured in a series of animal cell culture media consisting of a first, second and third media in order. The animal cell culture medium used in the present invention is a conventional animal cell culture medium employed in the art which may further contain additional ingredients and/or antibiotics according to the particular purpose of cultivation. Representative commercially available animal cell culture media include, but are not limited to, RPMI1640, MEM, a-MEM, IMDM or DMEM, preferably DMEM. Preferably, the animal cell culture medium is a high glucose medium which further contains D-glucose ranging from 3,500 to 5,500 mg/l and sodium pyruvate ranging from 50 to 200 mg/l and may contain additional ingredients and/or antibiotics according to the particular purpose of cultivation. In a preferred embodiment of the present invention, HG-DMEM (Gibco Cat. No. 12800-017) containing additional 4,500 mg/l of D-glucose and 110 mg/l of sodium pyruvate is employed as the high glucose medium.

First, the fresh mononuclear cells, freshly isolated from cord blood or the thawed mononuclear cells, are inoculated into the first animal cell culture medium at a concentration ranging from $1 \times 10^5$ to $1 \times 10^6$ cells/cm$^2$ and cultured at 37° C. under an atmosphere of 5% $CO_2$ for 1 to 2 weeks. Preferably, the culture medium is replaced with a fresh medium at an interval of 5 to 10 days.

At this time, the first animal cell culture medium is an high glucose medium further containing 10 to 20% FBS, 1 to 2 mM L-glutamine and 10 to 100 ng/ml GM-CSF. The cultivation in the first animal cell culture medium is a step for isolating only multipotent progenitor/stem cells from the pool of several types of stem cells in cord blood and it induces the multipotent progenitor/stem cells to form a multi-layer cell colony which grows adhered to the bottom of a culture flask. GM-CSF in the first animal cell culture medium plays the role of inducing the growth of multipotent progenitor/stem cells into the multi-layer cell colony.

When the multi-layer cell colony is formed, the first animal cell culture medium is replaced with the second animal cell culture medium which is the same as the first animal cell culture medium except that it lacks GM-CSF.

That is, the second animal cell culture medium is a high glucose medium further containing 10 to 20% FBS and 1 to 2 mM L-glutanine. The cultivation in the second animal cell culture medium is carried out by incubating at 37° C. under an atmosphere of 5% $CO_2$ for 1 to 2 weeks. At this time, the culture medium is replaced with a fresh medium at an interval of 5 to 10 days. This step is for removing non-attached cells and inducing metamorphosis of the multi-layer cell colony consisting of round-shaped cells into a mono-layer cell colony showing a fibroblast-like cell morphology.

After the second culture, when mono-layer cell colony forming cells are grown to 80 to 90% of adhesion, the culture medium is removed, and the cells are washed with PBS and treated with trypsin/EDTA, to recover the cells. The cells are inoculated into the third animal cell culture medium at a concentration ranging from $2 \times 10^4$ to $8 \times 10^4$ cells/cm$^2$ and cultured at 37° C. under an atmosphere of 5% $CO_2$ for 1 to 2 weeks to induce growth and proliferation of the cells into multipotent progenitor/stem cells. Preferably, the culture medium is replaced with a fresh medium at an interval of 3 to 5 days. The cultivation in the third animal cell culture medium is to maintain undifferentiated state of the cells cultured in the second animal cell culture medium and induce proliferation thereof. At this time, the third animal cell culture medium is the same as the first animal cell culture medium except that G-CSF is replaced with SCF and EGF. Preferably, the third animal cell culture medium is a high glucose culture medium further containing 10 to 20% FBS, 1 to 2 mM L-glutamine, 10 to 100 ng/ml of SCF and 5 to 50 ng/ml of EGF. SCF and EGF induce the proliferation of stem cells, and in particular, SCF plays the role of maintaining the multipotent progenitor/stem cells.

Figure 1:
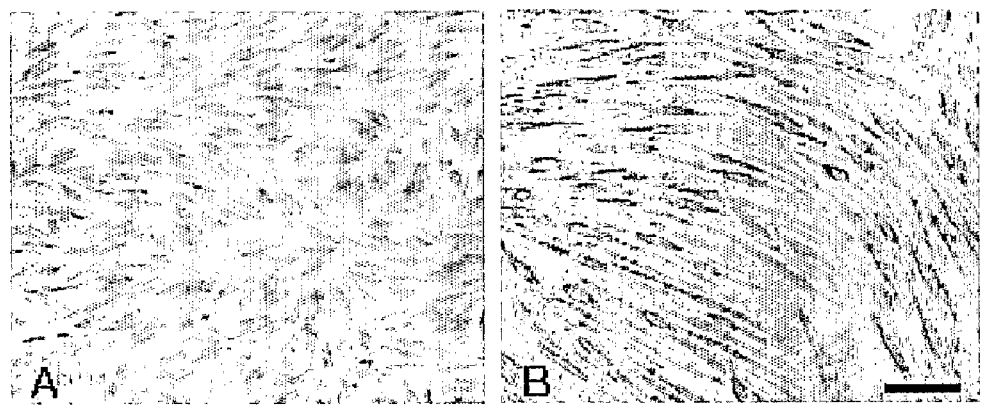
FIG. 1: photomicrographs of the multipotent progenitor/stem cells isolated and cultured from the cord blood-derived mononuclear cells.

The multipotent progenitor/stem cells thus isolated and cultured from the cord blood-derived mononuclear cells show the morphological characteristics of a fibroblast-like cell having a spindle shaped cell body (see FIG. 1). According to immunophenotyping by a flow cytometry, the multipotent progenitor/stem cells exhibit positive reactions against antibodies for hematopoietic antigens such as CD14, CD31 and CD45; negative reactions against antibodies for stem cell antigens such as CD34 and CD133; positive and partial positive reactions against antibodies for cell adhesion-relating antigens such as CD54 and CD166; negative and partial negative reactions against antibodies for MSC antigens such as CD73(SH3, SH4) and CD105(SH2); negative and partial positive reactions against antibodies for integrin protein antigens such as CD49a and CD104; a positive reaction against antibody for CD44; and negative reactions against CD62E and CD90(Thy-1)(see FIG. 2). Further, during the 12-week monitoring at an interval of 4 weeks, almost no change occurs in their immunophenotype profiles (see FIG. 3). These results suggest that the multipotent progenitor/stem cells isolated and cultured from the cord blood-derived mononuclear cells according to the method of the present invention belong to a hematopoietic cell family, but are differed from the previously reported hematopoietic stem cells or mesenchymal stem cells.

The cultured multipotent progenitor/stem cells show a doubling time of about 5 to 7 days and continuously proliferate over 12 weeks, to reach a massive amount of cells (see FIG. 4). Further, the cell cycle analysis of multipotent progenitor/stem cells has shown that about 20% of the total cells actively divide and participate in cell proliferation (see FIG. 5). These results suggest that the multipotent progenitor/stem cells in accordance with the present invention can continuously proliferate without losing their unique characteristics as progenitor/stem cells even if cultured over a long period of time to produce a large quantity of homogeneous cells.

Further, the present invention provides methods for inducing differentiation of the multipotent progenitor/stem cells into various types of cells as well as medium compositions used therein.

According to the methods of the present invention, it is possible to induce differentiation of the multipotent progenitor/stem cells into various types of cells including neurons, osteoblasts, myoblast, endothelial cells, hepatocytes and dendritic cells by culturing them in animal cell culture media having certain compositions under specific conditions depending on the target cell to be differentiated into.

In order to induce differentiation of the multipotent progenitor/stem cells into neurons, it is preferable to culture them in the animal cell culture medium further containing FBS, L-glutamine, retinoic acid, forskolin, nerve growth factor (NGF), a supplementary element mixture and beta-mercaptoethanol. The animal cell culture medium may further contain at least one of antibiotics selected from the group consisting of penicillin, streptomycin, kanamycin, ampicillin and amphotericin B. The supplementary element mixture as used herein refers to a mixture of ingredients that are conventionally used for animal cell culture in the art, which comprises 10 to 500 μg/ml of insulin, 1 to 20 mg/ml of transferrin, 0.1 to 2 μg/ml of progesterone, 1 to 5 mg/ml of putrascine and/or 0.1 to 5 μg/ml of selenite. Representative commercially available supplementary element mixtures include, but are not limited to, N2 Supplement, B27 Supplement and so on.

In a preferred embodiment of the present invention, the animal cell culture medium for inducing differentiation of the multipotent progenitor/stem cells into neurons is HG-DMEM supplemented with 0.1 to 2% FBS, 1 to 2 mM L-glutamine, 1 to 25 μM retinoic acid, 1 to 20 μM forskolin, 10 to 100 ng/ml NGF, 1×N2 Supplement(500 μg/ml of insulin, 10 μg/ml of transferrin, 0.63 μg/ml of progesterone, 1.6 mg/ml of putrascine and/or 0.52 μg/ml of selenite) and $1.0=10^{-6}$ to $1.0–10^{-5}$% beta-mercaptoethanol. The multipotent progenitor/stem cells are inoculated into the differentiation induction medium at a concentration ranging from $2\times10^4$ to $8\times10^4$ cells/cm$^2$ and cultured at 37° C. under an atmosphere of 5% $CO_2$ for 1 to 2 weeks.

The cells thus differentiated show the typical characteristics of neurons having well-spread neurodendrites (see FIG. 6). Analyses of fluorescence- or immunocytochemical staining, western blotting and reverse transcription polymerase chain reaction (RT-PCR) show that the differentiated cells exhibit positive signals for neuron-specific markers such as neuron specific enolase (NSE), neurofilament-L (NFL) and microtubule associated protein-1B (MAP-1B)(see FIGS. 7 and 8). An analysis to examine the cell type of the differentiated cells using specific markers for functional neurons reveals that the differentiated cells show positive reactions against tyrosine hydroxylase (TH), acetylcholin esterase (AchE) and glutamic acid decarboxylase (GAD)(see FIG. 9), which suggests that the multipotent progenitor/stem cells differentiate into dopaminergic neurons, cholinergic neurons and gabanergic neurons. Accordingly, it has been confirmed that the multipotent progenitor/stem cells successfully differentiate into neurons according to the method of the present invention. Further, the expression of meuroglial cell specific markers such as glial fibrillary acidic protein (GFAP) and myelin basic protein (MBP) are detected in the fluorescence- or immunocytochemical staining of the differentiated cells (see FIG. 10), which suggests that the multipotent progenitor/stem cells successfully differentiate into neuroglial cells according to the method of the present invention.

Further, in order to induce differentiation of the multipotent progenitor/stem cells into osteoblasts, it is preferable to culture them in the animal cell culture medium containing additional FBS, dexamethasone, ascorbate-2-phosphate and β-glycerophosphate. The animal cell culture medium may further contain at least one antibiotic selected from the group consisting of penicillin, streptomycin, kanamycin, ampicillin and amphotericin B.

Preferably, the animal cell culture medium for inducing differentiation into osteoblasts is HG-DMEM supplemented with 5 to 20% FBS, 0.1 to 1 μM dexamethasone, 10 to 100 μM ascorbate-2-phosphate and 5 to 20 mM β-glycerophosphate. The multipotent progenitor/stem cells are inoculated into the differentiation induction medium at a concentration ranging from $5\times10^4$ to $2\times10^5$ cells/cm$^2$ and cultured at 37° C. under an atmosphere of 5% $CO_2$ for 2 to 3 weeks, during which the culture medium is replaced with a fresh medium at an interval of 3 to 4 days.

Alkaline phosphatase (ALP) staining and RT-PCR show that ALP is strongly stained and the expression of osteoblast specific markers such as ALP and type I procollagen genes are detected in the differentiated cells in accordance with the present invention (see FIGS. 11 and 12), which demonstrates that the multipotent progenitor/stem cells successfully differentiate into osteoblasts according to the method of the present invention.

Further, in order to induce differentiation of the multipotent progenitor/stem cells into myoblasts, it is preferable to culture them in the animal cell culture medium containing additional bovine serum albumin (BSA) and 5-azacytidine. The animal cell culture medium may further contain at least one antibiotic selected from the group consisting of penicillin, streptomycin, kanamycin, ampicillin and amphotericin B.

Preferably, the animal cell culture medium for inducing differentiation into myoblasts is HG-DMEM supplemented with 5 to 10% BSA and 10 to 20 μM 5-azacytidine. The multipotent progenitor/stem cells are inoculated into the differentiation induction medium at a concentration ranging from $1\times10^5$ to $5\times10^5$ cells/well and cultured at 37° C. under an atmosphere of 5% $CO_2$ for 5 to 6 weeks, during which the culture medium is replaced with a fresh medium at an interval of 3 to 4 days.

RT-PCR and fluorescence immunocytochemical staining show that the expression of myoblast transcription markers such as MyoD, myogenin and myosin heavy chain genes are detected in the differentiated cells (see FIGS. 13 and 14), which proves that the multipotent progenitor/stem cells successfully differentiate into myoblasts according to the method of the present invention.

Further, in order to induce differentiation of the multipotent progenitor/stem cells into endothelial progenitor cells (EPCs), it is preferable to culture them in the animal cell culture medium containing additional FBS and vascular endothelial growth factor (VEGF). The animal cell culture medium may further contain at least one antibiotic selected from the group consisting of penicillin, streptomycin, kanamycin, ampicillin and amphotericin B.

Preferably, the animal cell culture medium for inducing differentiation into endothelial cells is HG-DMEM supplemented with 0.1 to 2% FBS and 10 to 100 ng/ml VEGF. The multipotent progenitor/stem cells are inoculated into the differentiation induction medium at a concentration ranging from $1\times10^5$ to $4\times10^5$ cells/cm$^2$ and cultured at 37° C. under an atmosphere of 5% $CO_2$ for 2 to 3 weeks, during which the culture medium is replaced with a fresh medium at an interval of 3 to 4 days.

According to immunophenotyping analysis, the differentiated cells show positive reactions against EPCs-relating antigens such as CD 14, CD31, CD45 and CD105(see FIG. 15). Further, they express EPCs specific markers such as VEGF receptor-1(Flt-1/VEGF-1), VEGF receptor-2(KDR/VEGFR-2), vascular endothelial cell-cadherin (VE-cadherin), endothelial cell nitric oxide synthase (ecNOS) and von Willebrand Factor (vWF) as well as ecNOS protein (see FIGS. 16 and 17). Further, it has been observed in fluorescence immunocytochemical staining and ac-LDL uptake analysis that most of the differentiated cells are capable of expressing vWF and UEA-1 proteins simultaneously with assimilating ac-LDL. It has been also found that the differentiated cells show the unique characteristics of endothelial cells such as tube formation and cytokine secretion (see FIGS. 18 to 20). Accordingly, these results demonstrate that the multipotent progenitor/stem cells successfully differentiate into endothelial progenitor cells according to the method of the present invention.

Further, in order to induce differentiation of the multipotent progenitor/stem cells into hepatocytes, it is preferable to culture them in the animal cell culture medium containing additional hepatocyte growth factor (HGF), oncostatin M and L-glutamine. The animal cell culture medium may further contain at least one antibiotics selected from the group consisting of penicillin, streptomycin, kanamycin, ampicillin and amphotericin B.

Preferably, the animal cell culture medium for inducing differentiation into hepatocytes is HG-DMEM supplemented with 10 to 100 ng/ml HGF, 5 to 50 ng/ml oncostatin M and 1 to 2 mM L-glutamine. The multipotent progenitor/stem cells are inoculated into the differentiation induction medium at a concentration ranging from $5 \times 10^4$ to $2 \times 10^5$ cells/cm and cultured at 37° C. under an atmosphere of 5% $CO_2$ for 2 to 4 weeks, during which the culture medium is replaced with a fresh medium at an interval of 3 to 7 days.

The differentiated cells express hepatocyte specific makers such as hepatocyte neuclear factor-1α(HNF-1α), cytokeratin-8(CK-8) and albumin as well as CK-8 and albumin proteins (see FIGS. 21 and 22), which suggests that the multipotent progenitor/stem cells successfully differentiate into hepatocytes according to the method of the present invention.

Further, in order to induce differentiation of the multipotent progenitor/stem cells into dendritic cells, it is preferable to successively culture them in two kinds of animal cell culture media, one being used for inducing immature differentiation, and the other, for inducing mature differentiation. The animal cell culture medium for inducing immature differentiation is a high glucose medium containing additional FBS, L-glutamine, GM-CSF and interleukin-4(IL-4), preferably HG-DMEM supplemented with 1 to 20% FBS, 1 to 2 mM L-glutamine, 10 to 1,000 ng/ml GM-CSF and 10 to 100 ng/ml IL-4. Further, the animal cell culture medium for inducing mature differentiation is the same as the former except that GM-CSF and IL-4 are replaced with tumor necrosis factor-α (TNF-α), IL-1β, IL-6 and prostaglandin E2, preferably HG-DMEM supplemented with 1 to 20% FBS, 1 to 2 mM L-glutamine, 1 to 100 ng/ml TNF-α, 1 to 100 ng/ml IL-1β, 100 to 10,000 U/ml IL-6 and 0.1 to 10 µg/ml prostaglandin E2. The animal cell culture media for immature and mature differentiation may further contain at least one antibiotic selected from the group consisting of penicillin, streptomycin, kanamycin, ampicillin and amphotericin B.

After the animal cell culture medium for inducing immature differentiation is distributed to each well of a 6-well culture plate, the multipotent progenitor/stem cells are inoculated into the well at a concentration ranging from $1 \times 10^5$ to $1 \times 10^7$ cells/well and cultured at 37° C. under an atmosphere of 5% $CO_2$ for 2 to 4 weeks. At this time, the culture medium is replaced with a fresh medium at an interval of 2 to 3 days. The cells thus cultured are transferred to the animal cell culture medium for inducing mature differentiation and cultured at 37° C. under an atmosphere of 5% $CO_2$ for 1 to 7 days.

The differentiated cells exhibit dextran-FITC uptake activity which is the unique characteristic of immature dendritic cells (see FIG. 23), and also show the immunophenotype profile having positive reactions against antibodies for dendritic cell antigen CD1a; simultaneous stimulus antigens such as CD40, CD80 and CD86; mature dendeitic cell antigen CD83; adhesion-relating antigen CD11c; and major histocompatibility complex type 2 HLA-DR, and negative reaction against antibody for T cell antigen CD8(see FIG. 24). Further, they are capable of inducing proliferation reaction in proportion to the stimulation dose against T lymphocytes in a mixed lymphocyte reaction (MLR)(see FIG. 25), which demonstrates that the multipotent progenitor/stem cells successfully differentiate into dendritic cells according to the method of the present invention.

Further, the present invention provides a cell composition for a cell therapy comprising the multipotent progenitor/stem cells isolated and cultured from the cord blood-derived mononuclear cells in accordance with the method of the present invention as an effective ingredient.

Since the multipotent progenitor/stem cells of the present invention are capable of differentiating into several types of cells including neurons, osteoblasts, myoblasts, endothelial cells, hepatocytes and dendritic cells, they can be effectively used for a cell therapy, a cell replacement therapy, an organ restoration technique or an organ production.

In particular, the cell composition comprising the multipotent progenitor/stem cells of the present invention as an effective ingredient can be used for treating Parkinson's disease, Alzheimer's diseases, quadriplegia resulting from spinal cord injury, leukemia, apoplexy, encephalophyma, juvenile-onset diabetes, cardiac infarction, hepatocirrhosis, muscle diseases, cardiomuscular diseases, liver diseases, blood diseases, the disruption and permanent functional disorder of osteoblasts and chondrocytes.

The cell composition of the present invention may be pharmaceutically formulated in accordance with any one of the conventional procedures. In preparing the formulation, the effective ingredient is preferably admixed or diluted with a carrier, excipient, or diluent. Examples of suitable carriers, excipients, or diluents are lactose, dextrose, sucrose, sorbitol, mannitol, glycine, polyethylene glycol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxybenzoates, talc, magnesium stearate, and mineral oil. The formulation may additionally include fillers, anti-agglutinating agents, lubricating agents, wetting agents, flavoring agents, emulsifiers, preservatives and the like. The composition of the invention may be formulated so as to provide a quick, sustained or delayed release of the effective ingredient after it is administered to a patient, by employing any one of the procedures well known in the art.

The cell composition of the present invention can be administered by injection (e.g., intramuscular, intravenous, intraperitoneal, subcutaneous), or by other methods such as infusion that ensure its delivery to the bloodstream in an effective form. The cell composition may also be administered by intratumoral, peritumoral, intralesional or perilesional routes, to exert local as well as systemic therapeutic effects. Local or intravenous injection is preferred.

A typical daily dose of the multipotent progenitor/stem cells as an effective ingredient may range from about $5\times10^5$ to $2\times10^7$ cells/kg body weight, preferably $1\times10^6$ to $1\times10^7$ cells/kg body weight, and can be administered in a single or in multiple doses. However, it should be understood that the amount of the active ingredient actually administered may be determined in light of various relevant factors, including the condition to be treated; the chosen route of administration; the age, sex and body weight of the individual patient; and the severity of the patient's symptom. Therefore, the above doses are not intended to limit the scope of this invention in any way.

The following Examples are intended to further illustrate the present invention without limiting its scope.

EXAMPLE 1

Isolation and Cultivation of Multipotent Progenitor/Stem Cells from Cord Blood-Derived Mononuclear Cells <1-1> Preparation of Cord Blood-Derived Mononuclear Cells 60 to 150 ml of umbilical cord blood was taken from the umbilical cord vein using a cord blood sampling bag (volume: 175 ml) containing 23 ml of anticoagulant CPDA-1 or a 50 ml syringe containing 5 ml of heparin before the placenta was separated from the uterus after parturition. All instruments used for the cord blood sampling were subject to aseptic treatment before use, and the sampling site was sterilized by alcohol or betadin.

In order to isolate mononuclear cells from the cord blood, 15 ml of the cord blood sample was distributed to a 50 ml conical tube within 24 hrs after the sampling. 15 ml of phosphate buffered saline (Dulbecco's PBS; Hyclone, SH300028.03) was added to the tube and mixed with the cord blood. 15 ml of Ficoll-Hypaque solution (Sigma, H8887, density; 1.077 g/ml) was gently overlayed onto the bottom of the conical tube, and the tube was subjected to centrifugation at 2,000 rpm, room temperature for 30 min, to fraction into an erythrocyte layer at the bottom part, a serologic layer at the upper part and a mononuclear cell layer therebetween. The mononuclear cell layer was separated therefrom using a Pasteur pipette and transferred to a new tube. 20 ml of PBS was added to the tube and mixed with the mononuclear cell layer. The tube was subjected to centrifugation at 2,000 rpm, room temperature for 10 min for washing. After a supernatant was removed from the tube, the mononuclear cell pellet was suspended in 40 ml of PBS, the survival rate and number of mononuclear cells in the suspension were measured, and then, the suspension was subjected to centrifugation at 2,000 rpm, room temperature for 10 min.

The mononuclear cell pellete thus obtained was suspended immediately in a basal medium and used for isolating and culturing multipotent progenitor/stem cells, or stored in a deep freezer.

For the deep freezing storage, the mononuclear cell pellete was suspended in the donor's own serum containing 10% DMSO (dimethyl sulfoxide) and distributed to 1.8 ml, freezing tubes at a concentration ranging from $4\times10^7$ to $6\times10^7$ cells/ml. After sealing the tube free of contaminants, the tube was frozen at $-100°$ C. in a program-controlled freezer and stored in a deep-freezer tank filled with liquid nitrogen.

When the frozen mononuclear cells were employed, the freezing tube carrying the mononuclear cells was subjected to rapid thawing in a $37°$ C. water bath. The thawed mononuclear cells were transferred to a conical tube and treated with a 10-volume amount of basal medium containing 10% BSA. The tube was subjected to centrifugation at 2,000 rpm, room temperature for 10 min to remove the supernatant, and the cell pellete thus obtained was used in the subsequent isolating and culturing procedures of multipotent progenitor/stem cells.

<1-2> Isolation and Cultivation of Multipotent Progenitor/Stem Cells from Cord Blood-Derived Mononuclear Cells 6 ml of a first animal cell culture medium was added to a T25 cell culture flask and the cord blood-derived mononuclear cells prepared in Example <1-1> was inoculated into the medium at a concentration ranging from $1\times10^5$ to $1\times10^6$ cells/cm². At this time, the first animal cell culture medium was HG-DMEM (Gibco, Cat. No. 12800-017, hereinafter, the same) supplemented with 10% FBS, 2 mM L-glutamine, 100 ng/ml GM-CSF and 100 U/ml penicillin-100 µg/ml streptomycin. The flask was incubated at $37°$ C. under an atmosphere of 5% $CO_2$ for 2 weeks. Whether the cells form a multi-layer cell colony that grew adhered to the bottom of the culture flask was monitored everyday. When the formation of the multi-layer cell colony was observed, the first animal cell culture medium was replaced with a second animal cell culture medium lacking GM-CSF in the first animal cell culture medium, and the cells were further cultured for 2 weeks, wherein the second animal cell culture medium was HG-DMEM supplemented with 10 FBS, 2 mM L-glutamine and 100 U/ml penicillin-100 µg/ml streptomycin. Through this cultivation in the second animal cell culture medium, non-attached cells were removed, while the multi-layer cell colony metamorphosed into a mono-layer cell colony showing a fibroblast-like cell morphology. Once the cells forming the mono-layer cell colony grew to 80 to 90% of adhesion, the second animal cell culture medium was discarded, the cells were washed with PBS, and, then, treated with 0.25% trypsin/EDTA. In order to maintain undifferentiated state of the cells and induce proliferation thereof, the cells thus obtained were inoculated into a new T25 culture flask containing a third animal cell culture medium at a concentration ranging from $2\times10^4$ to $8\times10^4$ cells/cm², and cultured at $37°$ C. under an atmosphere of 5% $CO_2$ for 1 week, wherein the third animal cell culture medium was HG-DMEM supplemented with 10% FBS, 2 mM L-glutamine, 10 ng/ml SCF, 10 ng/ml EGF and 100 U/ml of penicillin-100 µg/ml streptomycin.

The observation of the cultured cells according to the above method with a light microscope showed that the cultured cells have the unique characteristics of fibroblast-like cells having a spindle shaped cell body (FIG. 1).

EXAMPLE 2

Characterization of Multipotent Progenitor/Stem Cells Isolated and Cultured from Cord Blood-Derived Mononuclear Cells For immunophenotyping the multipotent progenitor/stem cells prepared from the cord blood-derived mononuclear cells in Example 1, the cultured cells were treated with 0.05% trypsin solution to detach them from the culture flask, and the detached cells were washed twice with PBS. The cells were suspended in PBS at a concentration of $5\times10^5$ cells/200 µl, 10 µl of each antibody was added thereto, and the flask was kept in a darkroom for 15 min. Then, the cells were washed twice with PBS for flow cytometry (Becton Dickinson), mixed with 500 µl of the same PBS, and subjected to immunophenotyping by a flow cytometry (FACScan, Becton Dickinson). At this time, PE- or FITC-conjugated CD14, CD31, CD34, CD44, CD45, CD49a, CD54, CD62E, CD73, CD90, CD104 (stated above, BD Sciences), CD105(Ancell Co.), CD133 (Miltenyi Biotec) and CD166(Ancell Co.) antibodies for FACS were employed.

The multipotent progenitor/stem cells isolated and cultured from the cord blood-derived mononuclear cells according to the method of the present invention indeed showed the immunophenotype profile having positive reactions against antibodies for CD 14, CD31, CD44, CD45 and CD54 antigens; negative reactions against antibodies for CD34, CD49a, CD62E, CD73, CD90 and CD133 antigens; and partial positive reactions against antibodies for CD104, CD105 and CD166 antigens (FIG. 2).

Figure 3A:
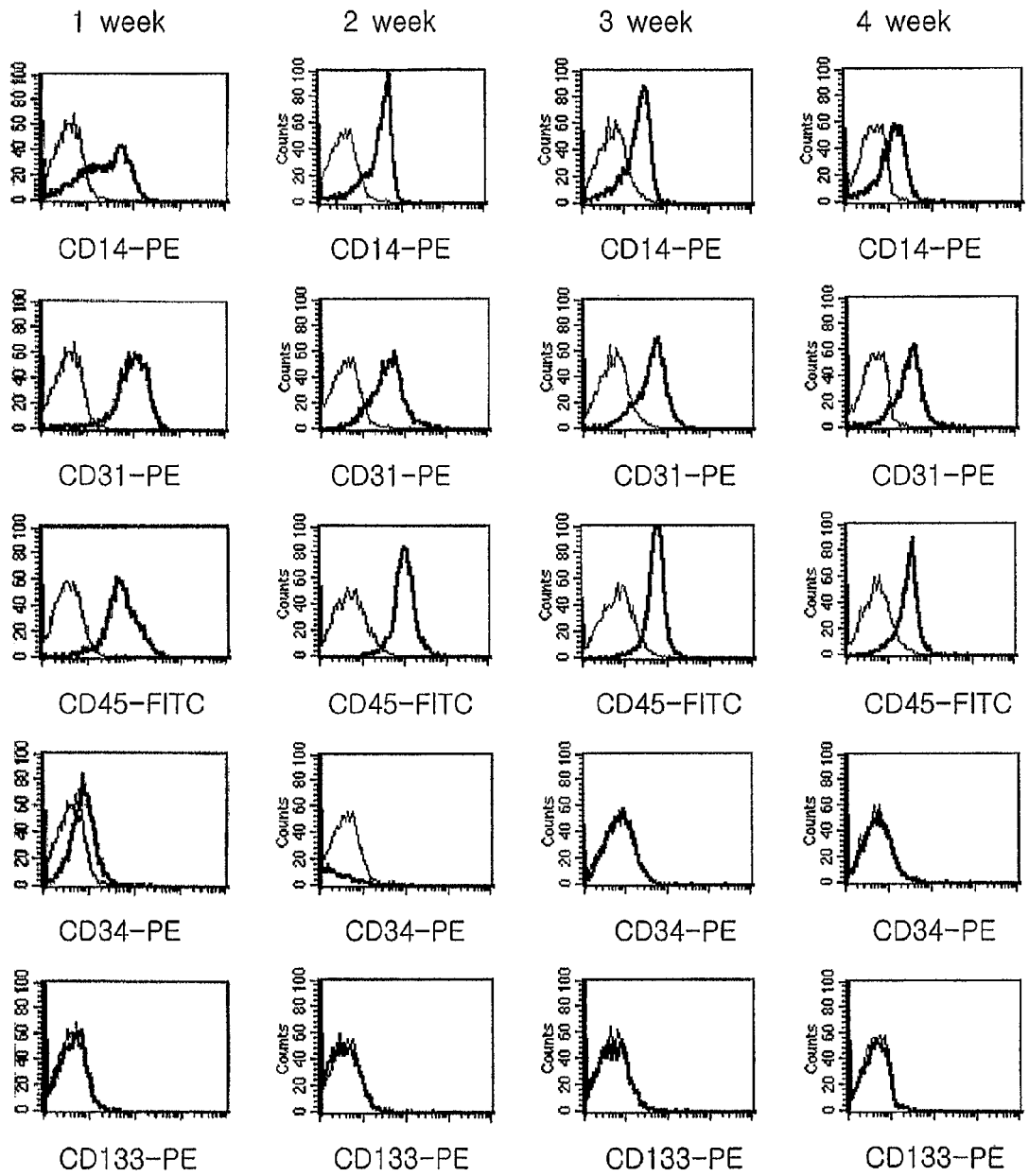
Figure 3B:
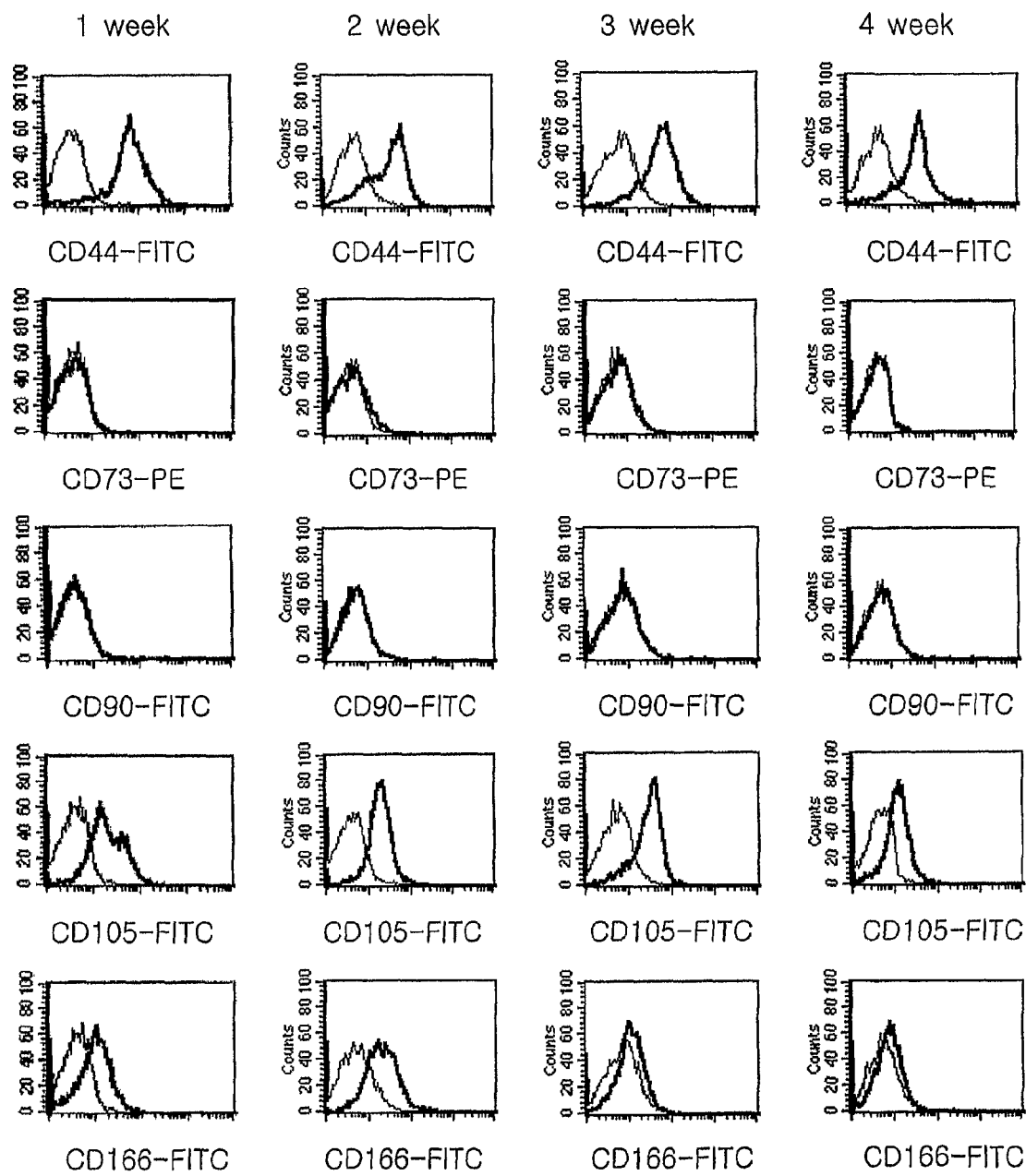

Further, in order to monitor the change in the immunophenotype profiles depending on a time course of culturing the multipotent progenitor/stem cells, the cells were cultured for 12 weeks and subjected to immunophenotyping at an interval of 4 weeks during the cultivation according to the same method as described above. The results showed that there was little decline in the expression of antigen such as CD105, but they showed the constant immunophenotype profile during the cultivation (FIGS. 3a and 3b).

In order to analyze the proliferation rate and cell cycle of the multipotent progenitor/stem cells prepared in Example 1, they were treated with 0.05% trypsin solution to detach them from the culture flask, the detached cells were washed twice with PBS, and then, subjected to cell counting according to a trypan blue exclusion method. Then, the cells were fixed by treating with 70% ethanol at 4° C. for 1 hr. The fixed cells were treated with CycleTEST PLUS DNA (BD Science) reagent to label them with 125 µg/ml of propidium iodine and their DNA content was measured with a flow cytometry (FACS Vantage, Becton Dickinson) to determine the cell cycle.

It has been found that the multipotent progenitor/stem cells isolated and cultured from the cord blood-derived mononuclear cells according to the method of the present invention continuously proliferate up to 12 weeks, leading to an increased cell mass about 25 to 30-fold higher than the initial mass, and about 20% (S phase+G2/M phase) of the total cells actively divided (FIGS. 4 and 5).

EXAMPLE 3

Differentiation of Cord Blood-Derived Multipotent Progenitor/Stem Cells into Neurons <3-1> Induction of Differentiation into Neurons In order to confirm whether the multipotent progenitor/stem cells obtained in Example 1 are capable of differentiating into various types of cells, they were subjected to induction of differentiation into neurons, as follows. The multipotent progenitor/stem cells were inoculated into an animal cell culture medium for inducing differentiation into neurons at a concentration of $4 \times 10^4$ cells/cm$^2$, and cultured for 1 to 2 weeks, wherein the differentiation induction medium was HG-DMEM supplemented with 1% FBS, 2 mM L-glutamine, 10 µM retinoic acid, 10 µM folskolin, 100 ng/ml NGF, 1×N2 supplement (Gibco BRL), 0.00001% beta-mercaptoethanol and 100 U/ml penicillin-100 µg/ml streptomycin.

<3-2> Confirmation of Differentiation into Neurons

As a result of observing with a light microscope whether the cord blood-derived multipotent progenitor/stem cells differentiate into neurons according to the method of Example <3-1>, it has been found that the differentiated cells show the typically morphological characteristics of neurons having neurodendrites, which demonstrates that the multipotent progenitor/stem cells successfully differentiated into neurons with the course of differentiation induction time accordance with the present invention.

Further, in order to examine whether the differentiated cells express a neuron specific marker, they were subjected to fluorescence- or immunocytochemical staining and western blotting. For the immunocytochemical staining, the differentiated cells grown on a slide glass were fixed with 4% paraformaldehyde (pH 7.4) for 10 min and washed three times with PBS (5 min per wash). After washing, about 30 to 50 µl of a blocking solution was dropped onto the stained surface of the cells and the slide glass was kept at 37° C. for about 1 hr to block non-specific reactions. The cells were reacted with a primary antibody at 37° C. for about 1 to 2 hrs and washed three times with PBS (about 5 min per wash). After washing, the cells were reacted with a secondary antibody at 37° C. for about 1 hr and washed with three times PBS (about 5 min per wash). After the antibody reaction was completed, the cells were subjected successively to ethanol treatment in a concentration-gradient manner (low→high) to induce intracellular dehydration, stained with xylene, subjected to mounting using a poly-mount solution, and then, observed with a light microscope (?). For the fluorescence immunocytochemical staining, the cells were subjected to mounting using 90% glycerol after the antibody reaction was completed and observed with a fluorescence microscope.

For the western blotting, after the culture medium was removed from the flask, the cells were washed, mixed with about 300 µl of RIPA buffer, and comminuted by using a scrapper. The comminuted cells were subjected to centrifugation at 4° C., 13,000 rpm for about 10 min, and the supernatant was separated. The supernatant was subjected to protein quantification and used for western blotting. About 30 to 80 µg/well of the protein was electrophorsed on a gel using a mini-gel electrophoretic apparatus and the protein separated on the gel was transferred to a PVDF membrane (Amersham Bioscience) to obtain a blot. The blot was soaked in Tris-buffered saline (TBS) containing 5% BSA for 1 hr to block non-specific reactions and washed with TBS. After washing, the blot was treated with a primary antibody at 4° C. for about 12 hrs and washed three times with TBS (about 10 min per wash). The blot was reacted with a secondary antibody at room temperature for about 1 hr and washed three times with TBS for about 10 min. After the antibody reaction was completed, the blot was soaked in an ECL solution to induce color development, and exposed to sensitize an X-ray film in a darkroom to examine the protein expression.

For the fluorescence- or immunocytochemical staining and western blotting, anti-NSE (Santa Cruz Biotechnology), MAP-1B (Santa Cruz Biotechnology), NF-L (Santa Cruz Biotechnology), TH (Santa Cruz Biotechnology), AchE (Chemicon International), GAD (Santa Cruz Biotechnology), GFAP (Santa Cruz Biotechnology) or MBP (Chemicon International) antibody was employed as the primary antibody and a peroxidase-conjugated anti-goat, anti-mouse or anti-rabbit antibody (Santa Cruz Biotechnology) was employed as the secondary antibody.

It was found that the cells differentiated from the cord blood-derived multipotent progenitor/stem cells strongly expressed neuron specific markers such as MAP-1B, NF-L and NSE (FIGS. 7 and 8), which suggests that the differentiation of multipotent progenitor/stem cells into neurons are successfully induced according to the method of the present invention. Further, the multipotent progenitor/stem cells differentiated into several types of neurons including dopaminergic neurons showing TH positive reaction, cholinergic neurons showing AchE positive reaction, and gabanergic neurons showing GAD positive reaction (FIG. 9). The differentiated cells showed positive reactions against GFAP, an astrocyte marker, and MBP, an oligodendrocyte marker (FIG. 10), which demonstrates that the multipotent progenitor/stem cells are capable of differentiating into neuroglial cells under the condition for inducing neuronal differentiation in accordance with the present invention.

EXAMPLE 4

Differentiation of Cord Blood-Derived Multipotent Progenitor/Stem Cells into Osteoblasts <4-1> Induction of Differentiation into Osteoblasts The miltipotent progenitor/stem cells prepared in Example 1 was treated with 0.05% trypsin/EDTA to detach them from the culture flask, and the detached cells were suspended in an animal cell culture medium for inducing differentiation into osteoblasts, wherein the animal cell culture medium was HG-DMEM supplemented with 10% BSA(Gibco), 0.1 µM dexamethasone, 100 µM ascorbate-2-phosphate, 10 mM β-glycerophosphate and 100 U/ml penicillin-100 µg/ml streptomycin. One week after the cell suspension was distributed into a 6-well plate at a concentration of $4 \times 10^5$ cells/well, the animal cell culture medium was added to the well and the well plate was incubated at 37° C. under an atmosphere of 5% $CO_2$ for 2 weeks. The culture medium was replaced with a fresh one at an interval of 3 to 4 days.

<4-2> Confirmation of Differentiation into Osteoblasts

In order to confirm the differentiation of multipotent progenitor/stem cells into osteoblasts, the differentiated cells were stained with an alkaline phosphatase (ALP) dye which selectively stains osteoblasts, as follows. First, the culture medium was discarded from the well plate and the cells were washed with ALP buffer. 1 ml of ALP dye (mixture of 1 mg/ml naphthol AS-TR phosphate and 2 mg/ml Fast red violet LB at a ratio of 10:1) was added to each well and the well plate was kept at 37° C. under an atmosphere of 5% $CO_2$ for 30 min. After the staining was completed, the ALP dye was removed from the well plate and the well plate was washed three times with PBS. 1 ml of 100% cold alcohol was added to each well and the well plate was kept in a cold chamber for 30 min to fix the cells. After the alcohol was removed therefrom and the well plate was washed twice with distilled water, the well plate was dried in air and observed with a fluorescence microscope. It was found that ALP stained only the cells differentiated from the cord blood-derived multipotent progenitor/stem cells (FIG. 11), which suggests that the differentiation of multipotent progenitor/stem cells into osteoblasts was successfully induced according to the method of the present invention.

Also examined was whether the multipotent progenitor/stem cells can differentiate into osteoblasts by reverse transcription-polymerse chain reaction (RT-PCR). After inducing the differentiation into osteoblasts, $1 \times 10^6$ to $1 \times 10^7$ cells were treated with 1 ml of Trizol (Invitrogen Inc.) for 5 min to induce cell lysis, and then, treated with 200 µl of chloroform. The resulting mixture was subjected to centrifugation at 15,000 rpm for 15 min to obtain a supernatant containing RNA. The supernatant was transferred to a new tube and 500 µl of isopropanol per 1 ml of Trizol was added thereto to precipitate RNA. RNA pellet thus obtained was washed with 75% cold ethanol, dried in air, dissolved in triple-distilled water containing DEPC at a suitable concentration, and used as a template for RT-PCR.

RNA thus obtained was kept at 65° C. for 5 min to remove a secondary structure. The RT-PCR reaction mixture was prepared by mixing 5 µl of 6×RT-PCR buffer, 2 µl of 2.5 mM dNTP, 1 µl of oligo d(T) primer (500 ng/µl), 0.5 µl of RNase inhibitor, 2 µg of template RNA and 1 µl of reverse transcriptase (200 U/µl; Promega), and adjusting the final volume to 30 µl with triple-distilled water containing DEPC. RT-PCR was conducted under the condition of 5 min at 94° C. to inactivate reverse transcriptase after the initial reaction of 90 min at 42° C., to synthesize cDNA used as a template for the subsequent PCR.

PCR was carried out using the following oligonucleotide primers that are designed to have complementary sequences to osteoblast specific genes: a primer pair of SEQ ID Nos: 1 and 2 specific for ALP gene; and a primer pair of SEQ ID Nos: 3 and 4 specific for type I procollagen gene. The PCR reaction mixture was prepared by mixing 1 gt of each primer (10 pmole), 2 µl of 2.5 mM dNTP mixture, 2.5 µl of 10×Taq DNA polymerase buffer (containing sodium chloride), 2 µl of template cDNA and 0.1 µl of Taq DNA polymerase (5 U/µl, Bioquest) and adjusting the final volume to 25 µl with triple-distilled water. PCR was conducted under the condition of 35 cycles of 60 sec at 94° C., 60 sec at the annealing temperature for each primer pair, and 60 sec at 72° C. after the initial denaturation (4 min at 94° C.) using a DNA thermocycler (Perkin-Elmer). At this time, the primer annealing temperature was 46° C. for ALP and 49° C. for type I procollagen.

It was found that the osteoblast specific markers such as ALP and type I procollagen were expressed in the cells differentiated from the cord blood-derived multipotent progenitor/stem cells in accordance with the present invention (FIG. 12).

EXAMPLE 5

Differentiation of Cord Blood-Derived Multipotent Progenitor/Stem Cells into Myoblasts <5-1> Induction of Differentiation into Myoblasts The miltipotent progenitor/stem cells prepared in Example 1 were treated with 0.05% trypsin/EDTA to detach them from the culture flask and the detached cells were suspended in an animal cell culture medium for inducing differentiation into myoblasts, wherein the culture medium was HG-DMEM supplemented with 10% BSA(Gibco), 10 µM 5-azacytidine and 100 U/ml penicillin-100 µg/ml streptomycin. One week after the cells were distributed into a 6-well plate at a concentration of $5 \times 10^5$ cells/well, the culture medium was added to the well and the well plate was incubated at 37° C. under an atmosphere of 5% $CO_2$ for 6 weeks. The culture medium was replaced with a fresh one at an interval of 3 to 4 days.

<5-2> Confirmation of differentiation into myoblasts

The differentiation of multipotent progenitor/stem cells into myoblasts was examined by RT-PCR according to the same method as described in Example 4. PCR was carried out using the following oligonucleotide primers that are designed to have complementary sequences to myoblast specific genes: a primer pair of SEQ ID Nos: 5 and 6 specific for myoD gene; a primer pair of SEQ ID Nos: 7 and 8 specific for myogenin gene; and a primer pair of SEQ ID Nos: 9 and 10 specific for myosin heavy chain gene. The primer annealing temperature was 48° C. for myoD, 48° C. for myogenin, and 56° C. for myosin heavy chain.

It was found that myoblast transcription factors such as myoD and myogenin, and a myosin functional regulator such as myosin heavy chain gene were expressed in the cells differentiated from the cord blood-derived multipotent progenitor/stem cells in accordance with the present invention (FIG. 13).

Further, the results of fluorescence immunocytochemical staining according to the same method as described in Example 3 showed that myoD and myogenin stained the cells differentiated from the multipotent progenitor/stem cells (FIG. 14), which suggests that the multipotent progenitor/stem cells successfully differentiated into myoblasts according to the method of the present invention.

EXAMPLE 6

Differentiation of Cord Blood-Derived Multipotent Progenitor/Stem Cells into Endothelial Cells <6-1> Induction of Differentiation into Endothelial Cells Only the floating cells were taken from the multipotent progenitor/stem cells cultured in Example 1 and suspended in an animal cell culture medium for is inducing differentiation into endothelial cells which was HG-DMEM supplemented with 1% FBS, 10 ng/ml VEGF and 100 U/ml penicillin-100 µg/ml streptomycin. The suspension was distributed into a 6-well plate at a concentration of $4 \times 10^5$ cells/well and the well plate was incubated at 37° C. under an atmosphere of 5% $CO_2$ for 2 weeks. The culture medium was replaced with a fresh one at an interval of 3 to 4 days.

<6-2> Confirmation of Differentiation into Endothelial Cells

Immunophenotyping of the cells thus cultured in Example <6-1> was carried out by a flow cytometry according to the same method as described in Example 2. As illustrated in FIG. 15, the cells showed the inmunophenotype profile having positive reactions against antibodies for CD31, CD34, CD105, CD14 and CD45 antigens and a negative reaction against an antibody for CD133 antigen.

Further, RT-PCR was conducted to examine the differentiation into endothelial cells according to the same method as described in Example 4. PCR was carried out by using the following oligonucleotide primers that are designed to have complementary sequences to endothelial cell specific genes: a primer pair of SEQ ID Nos: 11 and 12 specific for Flt-1/VEGFR-1 gene; a primer pair of SEQ ID Nos: 13 and 14 specific for KDR (kinase insert domain receptor)/VEGFR-2 gene; a primer pair of SEQ ID Nos: 15 and 16 specific for ecNOS gene; a primer pair of SEQ ID Nos: 17 and 18 specific for VE-cadherin gene; a primer pair of SEQ ID Nos: 19 and 20 specific for vWF gene; and a primer pair of SEQ ID Nos: 21 and 22 specific for β-actin gene. The primer annealing temperature was 56° C. for all the above mentioned genes.

As a result, the endothelial cell specific markers such as Flt-1/VEGFR-1, KDR/VEGFR-2, ecNOS, VE-cadherin and vWF genes were detected in the differentiated cells from the cord blood-derived multipotent progenitor/stem cells in accordance with the present invention (FIG. 16).

In order to confirm the differentiation of multipotent progenitor/stem cells into endothelial cells, the expression of ecNOS was analyzed by western blotting according to the same method as described in Example 3, and the result showed that ecNOS was expressed in the differentiated cells from the multipotent progenitor/stem cells (FIG. 17).

Further, the expression of vWF and UEA-1 proteins in the differentiated cells was analyzed by the fluorescence immunocytochemical staining according to the same method as described in Example 3, and their ac-LDL uptake activity was examined as follows. The differentiated cells were treated with ac-LDL at a concentration of 50 ng/ml and kept at 37° C. under an atmosphere of 5% $CO_2$ for 4 hrs. After removing the reagent, the cells were washed three times with PBS. The cells were treated with 4% formalin for 30 min to fix them and observed by a fluorescence microscope. As a result, it has been found that ac-LDL is incorporated into the differentiated cells and vWF and UEA-1 are strongly detected therein (FIG. 18).

In order to confirm whether the differentiated cells function as endothelial cells, their tube formation activity was examined. First, 200 µl of matrigel was poured into each well and the well plate was kept at 37° C. under an atmosphere of 5% $CO_2$ for 30 min to solidify. The differentiated cells were inoculated into the well plate at a concentration of $2 \times 10^5$ cells/well and monitored their tube formation for 24 hrs. As a result, it has been found that about 50 to 60% of the total cells involve in the tube formation (FIG. 19).

Also examined was whether the differentiated cells secrete VEGF by using a ELISA kit (Quantikine, R&D systems) according to the manufacturer's instruction. As a result, the differentiated cells secreted 900 pg or more of VEGF (FIG. 20), which suggests that the cord blood-derived multipotent progenitor/stem cells successfully differentiate into endothelial cells in accordance with the present invention.

EXAMPLE 7

Differentiation of Cord Blood-Derived Multipotent Progenitor/Stem Cells into Hepatocytes <7-1> Induction of Differentiation into Hepatocytes The multipotent progenitor/stem cells cultured in Example 1 were inoculated into an animal cell culture medium for inducing differentiation into hepatocytes at a concentration of $1 \times 10^5$ cells/cm² and cultured for 2 to 4 weeks, wherein the animal cell culture medium was HG-DMEM supplemented with 25 ng/ml hepatocyte growth factor (HGF), 20 ng/ml oncostatin M (OSM), 2 mM L-glutamine and 100 U/ml penicillin-100 µg/ml streptomycin, and the matrigel coated well plate was employed.

<7-2> Confirmation of Differentiation into Hepatocytes

RT-PCR was conducted to analyze the differentiation of multipotent progenitor/stem cells into hepatocytes according to the same method as described in Example 4. PCR was carried out using the following oligonucleotide primers that are designed to have complementary sequences to hepatocyte specific genes: a primer pair of SEQ ID NOs: 23 and 24 specific for HNF1-alpha gene; a primer pair of SEQ ID NOs: 25 and 26 specific for cytokeratin-8 gene; and a primer pair of SEQ ID NOs: 27 and 28 specific for albumine gene. The primer annealing temperature was 58° C. for HNF1-alpha and CK-8, and 62° C. for albumin.

FIG. 21 shows that the differentiated cells express the hepatocyte specific markers such as HNF1-alpha, CK-8 and albumin genes.

Further, the immunocytochemical staining exhibited that CK-8 and albumin were stained in the differentiated cells (FIG. 22), which demonstrates that the cord blood-derived multipotent progenitor/stem cells successfully differentiate into hepatocytes according to the method of the present invention.

EXAMPLE 8

Differentiation of Cord Blood-Derived Multipotent Progenitor/Stem Cells into Dendritic Cells <8-1> Induction of differentiation into dendritic cells The miltipotent progenitor/stem cells prepared in Example 1 was treated with 0.05% trypsin/EDTA to detach from the culture flask and distributed into a 6-well plate at a concentration of $5 \times 10^5$ cells/well. An animal cell culture medium for inducing immature differentiation into dendritic cells was added to each well and the well plate was incubated at 37° C. under an atmosphere of 5% $CO_2$ for 5 days, wherein the culture medium was HG-DMEM supplemented with 10% FBS, 2 mM L-glutamine, 100 ng/ml GM-CSF, 20 ng/ml IL-4 and 100 U/ml penicillin-100 µg/ml streptomycin. The culture medium was replaced with a fresh one at an interval of 2 to 3 days. The cells were transferred to an animal cell culture medium for inducing mature differentiation into dendritic cells and further cultured at 37° C. under an atmosphere of 5% $CO_2$ for 2 days, wherein the animal cell culture medium was HG-DMEM supplemented with 10% FBS, 2 mM L-glutamine, 10 ng/ml TNF-α, 10 ng/ml IL-1β, 1,000 U/ml IL-6, 1 µg/ml prostaglandin E2 and 100 U/ml penicillin-100 µg/ml streptomycin.

<8-2> Confirmation of Differentiation into Dendritic Cells

In order to confirm the differentiation of multipotent progenitor/stem cells into dendritic cells, dextran-FITC uptake activity of the differentiated cells was measured as follows. The floating cells were recovered from the culture flask and washed twice with PBS. The cells were suspended in FBS free culture medium at a concentration of $2 \times 10^5$ cells/200 µl and 10 µl of 20 mg/ml dextran-FITC (Sigma) was added thereto. At this time, a control group was reacted at 4° C., and a test group was reacted at 37° C. for 2 hrs in a darkroom.

Figure 23:
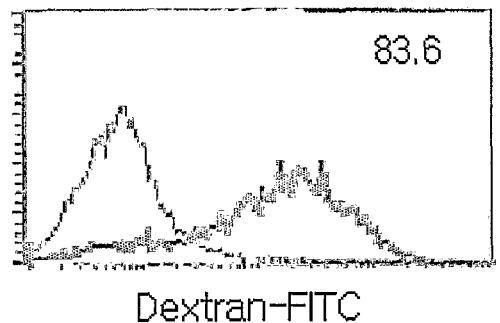

After the dark reaction was completed, the cells were washed twice with PBS for flow cytometry (Becton Dickinson), mixed with 500 µl of the same buffer, and, then, analyzed by a flow cytometry (FACScan, Becton Dickinson). As a result, the differentiated cells in accordance with the present invention assimilated most of dextran-FITC (FIG. 23).

Further, the differentiated cells were subjected to immunophenotyping by a flow cytometry according to the same method as described in Example 2. For the immunophenotyping, antibodies against a mononuclear cell antigen such as CD14; dendritic cell and langerhans cell antigens such as CD1a; a cell adhesion-relating antigen such as CD11c; T cell-relating antigen such as CD8; co-stimulatory antigens such as CD80, CD86 and CD40; a mature dendritic cell-relating antigen such as CD83; and MHC Class 2 HLA-DR (stated above, BD Sciences) were employed.

As illustrated in FIG. 24, the differentiated cells showed the immunophenotype profile having positive reactions against antibodies for CD1a, CD11c, CD40, CD80, CD86, CD83 and HLA-DR antigens, and a negative reaction against antibody for CD8 antigen.

Further, in order to examine the effect of the differentiated cells on inducing T lymphocyte proliferation, CD3+T lymphocytes were isolated from a blood sample using a CD3 magnetic particle solution (Miltenyl Biotech, Bergisch Glandbac, Germany). $5 \times 10^4$ cells/100 µl of T lymphocytes were mixed with the mature dendritic cells ranging from $1 \times 10^2$ to $1 \times 10^4$ cells/100 µl to adjust the mixed ratio of dendritic cells and T lymphocytes (stimulator: responder) to 1:5, 1:10, 1:50, 1:100 and 1:500, respectively, and the cell mixtures were distributed into a 96-well plate. The well plate was incubated at 37° C. under an atmosphere of 5% $CO_2$ for 4 days. At the $5^{th}$ day, 10 µl of BrdU (5-bromo-2'-dexoyuridine) solution(Roche) was added to each well and the well plate was further incubated at 37° C. under an atmosphere of 5% $CO_2$ for 24 hrs. T lymphocyte proliferation was measured by using an ELISA reader. As a result, it has been found that the mature dendritic cells differentiated from the multipotent progenitor/stem cells are capable of inducing proliferation against T lymphocytes in proportion to a stimulation dose (FIG. 25).

While the invention has been described with respect to the above specific embodiments, it should be recognized that various modifications and changes may be made to the invention by those skilled in the art which also fall within the scope of the invention as defined by the appended claims.

What is claimed is:

1. A method for isolating and culturing multipotent progenitor cells from cord blood-isolated mononuclear cells, which comprises culturing the cord blood-isolated mononuclear cells successively in:
   1) a first animal cell culture medium comprising fetal bovine serum (FBS), L-glutamine and granulocyte macrophage-colony stimulating factor (GM-CSF), in addition to inorganic salts, vitamins, and amino acids;
   2) a second animal cell culture medium which is the same as the first animal cell culture medium except for lacking GM-CSF; and
   3) a third animal cell culture medium which is the same as the first animal cell culture medium except that GM-CSF is replaced with stem cell factor (SCF) and epidermal growth factor (EGF).

2. The method of claim 1, wherein the animal cell culture medium further contains D-glucose and sodium pyruvate.

3. The method of claim 1, wherein the first animal cell culture medium contains 10 to 20% FBS, 1 to 2 mM L-glutamine, and 10 to 100 ng/ml GM-CSF; the second animal cell culture medium contains 10 to 20% FBS and 1 to 2 mM L-glutamine; and the third animal cell culture medium contains 10 to 20% FBS, 1 to 2 mM L-glutamine, SCF and EGF.

4. The method of claim 1, wherein the cultivation in the first animal cell culture medium is conducted by inoculating the mononuclear cells into the first animal cell culture medium and culturing at 37° C. under an atmosphere of 5% $CO_2$ for 1 to 2 weeks; the cultivation in the second animal cell culture medium is conducted by replacing the first animal cell culture medium by the second animal cell culture medium after confirming the formation of a multi-layer cell colony and further culturing at 37° C. under an atmosphere of 5% $CO_2$ for 1 to 2 weeks; and the cultivation in the third animal cell culture medium is conducted by inoculating the cells cultured in the second animal cell culture medium into the third animal cell culture medium after observing the metamorphosis of the multi-layer cell colony into a mono-layer cell colony and further culturing at 37° C. under an atmosphere of 5% $CO_2$ for 1 to 2 weeks.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: forward primer specific for alkaline phosphatase

<400> SEQUENCE: 1
acgtggctaa gaatgtcatc                                               20

<210> SEQ ID NO 2
<211> LENGTH: 19
<212> TYPE: DNA
<213> ORGANISM: Artificial Sequence
<220> FEATURE:
<223> OTHER INFORMATION: reverse primer specific for alkaline phosphatase

<400> SEQUENCE: 2
ctggtaggcg atgtcctta					19

<210> SEQ ID NO 3
<211> LENGTH: 18
<212> TYPE: DNA
<213> ORGANISM: Artificial Sequence
<220> FEATURE:
<223> OTHER INFORMATION: forward primer specific for type I procollagen

<400> SEQUENCE: 3
tgacgagacc aagaactg					18

<210> SEQ ID NO 4
<211> LENGTH: 20
<212> TYPE: DNA
<213> ORGANISM: Artificial Sequence
<220> FEATURE:
<223> OTHER INFORMATION: reverse primer specific for type I procollagen

<400> SEQUENCE: 4
cgatccaaac cactgaaacc					20

<210> SEQ ID NO 5
<211> LENGTH: 20
<212> TYPE: DNA
<213> ORGANISM: Artificial Sequence
<220> FEATURE:
<223> OTHER INFORMATION: forward primer specific for myoD

<400> SEQUENCE: 5
aatgtagcag gtgtaaccgt					20

<210> SEQ ID NO 6
<211> LENGTH: 20
<212> TYPE: DNA
<213> ORGANISM: Artificial Sequence
<220> FEATURE:
<223> OTHER INFORMATION: reverse primer specific for myoD

<400> SEQUENCE: 6
gcctttattt tgatcacctg					20

<210> SEQ ID NO 7
<211> LENGTH: 20
<212> TYPE: DNA
<213> ORGANISM: Artificial Sequence
<220> FEATURE:
<223> OTHER INFORMATION: forward primer specific for myogenin

<400> SEQUENCE: 7
cactacttct gtagcagggg					20

<210> SEQ ID NO 8
<211> LENGTH: 20
<212> TYPE: DNA
<213> ORGANISM: Artificial Sequence
<220> FEATURE:
<223> OTHER INFORMATION: reverse primer specific for myogenin

<400> SEQUENCE: 8
tctctcaaac cgtttcactt					20

```
<210> SEQ ID NO 9
<211> LENGTH: 20
<212> TYPE: DNA
<213> ORGANISM: Artificial Sequence
<220> FEATURE:
<223> OTHER INFORMATION: forward primer specific for myosin heavy chain

<400> SEQUENCE: 9
tgtgaatgcc aaatgtgctt                                              20

<210> SEQ ID NO 10
<211> LENGTH: 20
<212> TYPE: DNA
<213> ORGANISM: Artificial Sequence
<220> FEATURE:
<223> OTHER INFORMATION: reverse primer specific for myosin heavy chain

<400> SEQUENCE: 10
gtggagctgg gtatccttga                                              20

<210> SEQ ID NO 11
<211> LENGTH: 20
<212> TYPE: DNA
<213> ORGANISM: Artificial Sequence
<220> FEATURE:
<223> OTHER INFORMATION: forward primer specific for Flt-1/VEGFR-1

<400> SEQUENCE: 11
ggtcttacgg agtattgctg                                              20

<210> SEQ ID NO 12
<211> LENGTH: 20
<212> TYPE: DNA
<213> ORGANISM: Artificial Sequence
<220> FEATURE:
<223> OTHER INFORMATION: reverse primer specific for Flt-1/VEGFR-1

<400> SEQUENCE: 12
ctttcttttg ggtctctgtg                                              20

<210> SEQ ID NO 13
<211> LENGTH: 20
<212> TYPE: DNA
<213> ORGANISM: Artificial Sequence
<220> FEATURE:
<223> OTHER INFORMATION: forward primer specific for KDR/VEGFR-2

<400> SEQUENCE: 13
ggacctggcg gcacgaaata                                              20

<210> SEQ ID NO 14
<211> LENGTH: 20
<212> TYPE: DNA
<213> ORGANISM: Artificial Sequence
<220> FEATURE:
<223> OTHER INFORMATION: reverse primer specific for KDR/VEGFR-2

<400> SEQUENCE: 14
aggccggctc tttcgcttac                                              20

<210> SEQ ID NO 15
<211> LENGTH: 30
<212> TYPE: DNA
<213> ORGANISM: Artificial Sequence
<220> FEATURE:
<223> OTHER INFORMATION: forward primer specific for ecNOS
```

<400> SEQUENCE: 15
aagacatttt cgggctcacg ctgcgcaccc                                30

<210> SEQ ID NO 16
<211> LENGTH: 30
<212> TYPE: DNA
<213> ORGANISM: Artificial Sequence
<220> FEATURE:
<223> OTHER INFORMATION: reverse primer specific for ecNOS

<400> SEQUENCE: 16
tggggtaggc actttagtag ttctcctaac                                30

<210> SEQ ID NO 17
<211> LENGTH: 19
<212> TYPE: DNA
<213> ORGANISM: Artificial Sequence
<220> FEATURE:
<223> OTHER INFORMATION: forward primer specific for VE-cadherin

<400> SEQUENCE: 17
gatgcagagg ctcatgatg                                            19

<210> SEQ ID NO 18
<211> LENGTH: 20
<212> TYPE: DNA
<213> ORGANISM: Artificial Sequence
<220> FEATURE:
<223> OTHER INFORMATION: reverse primer specific for VE-cadherin

<400> SEQUENCE: 18
cttgcgactc acgcttgact                                           20

<210> SEQ ID NO 19
<211> LENGTH: 20
<212> TYPE: DNA
<213> ORGANISM: Artificial Sequence
<220> FEATURE:
<223> OTHER INFORMATION: forward primer specific for vWF

<400> SEQUENCE: 19
caccgtttgc ccacccttcg                                           20

<210> SEQ ID NO 20
<211> LENGTH: 20
<212> TYPE: DNA
<213> ORGANISM: Artificial Sequence
<220> FEATURE:
<223> OTHER INFORMATION: reverse primer specific for vWF

<400> SEQUENCE: 20
gcccactggg agccgacact                                           20

<210> SEQ ID NO 21
<211> LENGTH: 19
<212> TYPE: DNA
<213> ORGANISM: Artificial Sequence
<220> FEATURE:
<223> OTHER INFORMATION: forward primer specific for beta-actin

<400> SEQUENCE: 21
tgaaccaggc ttcagcatc                                            19

<210> SEQ ID NO 22
<211> LENGTH: 20

```
<212> TYPE: DNA
<213> ORGANISM: Artificial Sequence
<220> FEATURE:
<223> OTHER INFORMATION: reverse primer specific for beta-actin

<400> SEQUENCE: 22
ggacttcgag caagatatgg                                              20

<210> SEQ ID NO 23
<211> LENGTH: 25
<212> TYPE: DNA
<213> ORGANISM: Artificial Sequence
<220> FEATURE:
<223> OTHER INFORMATION: forward primer specific for HNF1-alpha

<400> SEQUENCE: 23
ttctaagctc agccagctgc agacg                                        25

<210> SEQ ID NO 24
<211> LENGTH: 25
<212> TYPE: DNA
<213> ORGANISM: Artificial Sequence
<220> FEATURE:
<223> OTHER INFORMATION: reverse primer specific for HNF1-alpha

<400> SEQUENCE: 24
gctgaggttc tccggctctt tcaga                                        25

<210> SEQ ID NO 25
<211> LENGTH: 20
<212> TYPE: DNA
<213> ORGANISM: Artificial Sequence
<220> FEATURE:
<223> OTHER INFORMATION: forward primer specific for cytokeratin-8

<400> SEQUENCE: 25
caatgccaag ctggaggatc                                              20

<210> SEQ ID NO 26
<211> LENGTH: 20
<212> TYPE: DNA
<213> ORGANISM: Artificial Sequence
<220> FEATURE:
<223> OTHER INFORMATION: reverse primer specific for cytokeratin-8

<400> SEQUENCE: 26
acctcaggct ggcaatgact                                              20

<210> SEQ ID NO 27
<211> LENGTH: 24
<212> TYPE: DNA
<213> ORGANISM: Artificial Sequence
<220> FEATURE:
<223> OTHER INFORMATION: forward primer specific for albumine

<400> SEQUENCE: 27
tgcttgaatg tgctgatgac aggg                                         24

<210> SEQ ID NO 28
<211> LENGTH: 25
<212> TYPE: DNA
<213> ORGANISM: Artificial Sequence
```

-continued

```
<220> FEATURE:
<223> OTHER INFORMATION: reverse primer specific for albumine

<400> SEQUENCE: 28
aaggcaagtc agcaggcatc tcatc                                                25
```